(12) United States Patent
Lewis

(10) Patent No.: US 6,473,805 B2
(45) Date of Patent: Oct. 29, 2002

(54) METHOD AND APPARATUS FOR INTERGRATING WIRELESS AND NON-WIRELESS DEVICES INTO AN ENTERPRISE COMPUTER NETWORK USING AN INTERFACING MIDWARE SERVER

(75) Inventor: Daniel E. Lewis, The Woodlands, TX (US)

(73) Assignee: Telxon Corporation, Akron, OH (US)

(*) Notice: Subject to any disclaimer, the term of this patent is extended or adjusted under 35 U.S.C. 154(b) by 0 days.

(21) Appl. No.: 09/093,330

(22) Filed: Jun. 8, 1998

(65) Prior Publication Data

US 2001/0042135 A1 Nov. 15, 2001

(51) Int. Cl.$^7$ ................................................ G06F 15/16
(52) U.S. Cl. ....................... 709/246; 709/238; 709/249; 705/1; 705/3
(58) Field of Search ................................. 709/217–219, 709/223, 231, 238, 249, 250, 246, 311, 312; 705/1, 3, 79

(56) References Cited

U.S. PATENT DOCUMENTS

| | | | |
|---|---|---|---|
| 5,123,029 A | | 6/1992 | Bantz et al. ................. 375/133 |
| 5,446,736 A | | 8/1995 | Gleeson et al. ............. 370/473 |
| 5,646,389 A | * | 7/1997 | Bravman et al. ........... 235/385 |
| 5,717,737 A | | 2/1998 | Doviak et al. |
| 5,742,905 A | * | 4/1998 | Pepe et al. .................. 455/461 |
| 5,805,676 A | * | 9/1998 | Martino ........................ 379/93 |
| 5,857,201 A | * | 1/1999 | Wright, Jr. et al. ......... 707/104 |
| 5,987,103 A | * | 11/1999 | Martino ........................ 379/93 |
| 6,012,088 A | | 1/2000 | Li et al. ....................... 709/219 |
| 6,023,684 A | | 2/2000 | Pearson ........................ 705/35 |
| 6,044,382 A | * | 3/2000 | Martino ...................... 707/505 |
| 6,052,672 A | | 4/2000 | Foster .......................... 705/35 |
| 6,058,375 A | * | 5/2000 | Park ............................. 705/30 |
| 6,070,199 A | * | 5/2000 | Axtman et al. ................ 710/1 |
| 6,070,761 A | * | 6/2000 | Bloom et al. ................. 222/81 |
| 6,101,500 A | * | 8/2000 | Lau ............................. 707/103 |
| 6,130,892 A | * | 10/2000 | Short et al. ................. 370/401 |

OTHER PUBLICATIONS

Symbol Technologies Inc., Symbol Technologies Mobile Application Transaction (MAT) Server for SAP, Jan. 6, 1998, 5 pages.

\* cited by examiner

Primary Examiner—Mehmet B. Geckil
Assistant Examiner—Beatriz Prieto
(74) Attorney, Agent, or Firm—Renner, Otto, Boisselle & Sklar, LLP

(57) ABSTRACT

In an enterprise network system a plurality of software systems are integrated using an enterprise wide software management system and communicate with a plurality of clients. At least one of the clients is functionally represented by a plurality of subclients through a midware which is transparent to the software systems. Communication destined for any of the clients interfaced through the midware is received by the midware and converted to a format suitable for communication with one or more of the subclients prior to transmission thereto. Correspondingly, communications received from one or more subclients is converted to an appropriate format by the midware and forwarding to the assigned destination. Communications received by the midware is further monitored for fields which are tracked. Upon receiving communications having fields being tracked, the midware stores a least a portion of the communication in a report table.

38 Claims, 19 Drawing Sheets

| TASK # | DATA STRUCTURE RECEIVED BY MIDWARE | MIDWARE OPERATION |
|---|---|---|
| 001 | $(D_1, D_2, D_3, D_4)$ | TIME 1 - SELECT SUB-CLIENT TO PERFORM SUBTASK 1(SUBCLIENT 5a) ~ 85 |
| | | TIME 2 - SEND DATA STRUCTURE $(D_1, D_4)$ TO SUBCLIENT 5a ~ 86 |
| | | TIME 3 - RECEIVE DATA STRUCTURE $(S_1, S_2)$ FROM SUBCLIENT 5a ~ 87 |
| | | TIME 1 - SELECT SUB-CLIENT TO PERFORM SUBTASK 2 (SUBCLIENT 5b) ~ 88 |
| | | TIME 2 - SEND DATA STRUCTURE $(D_2, D_4)$ TO SUBCLIENT 5b ~ 89 |
| | | TIME 3 - RECEIVE DATA STRUCTURE $(S_3, S_4)$ FROM SUBCLIENT 5b ~ 90 |
| | | TIME 1 - MATCH $D_3$ TO $L_1$ ~ 92 |
| | | TIME 4 - SEND DATA STRUCTURE $(D_1, D_2, \text{SUBCLIENT 5a})$ TO REPORT TABLE ~ 93 |
| | | TIME 4 - SEND DATA STRUCTURE $(D_2, D_4, \text{SUBCLIENT 5b})$ TO REPORT TABLE ~ 94 |
| | | TIME 4 - SEND DATA STRUCTURE $(S_1, S_2, S_3, S_4)$ TO INITIALIZING SYSTEM ~ 95 |
| | | TIME 4 - SEND DATA STRUCTURE $(L_1, S_2, S_4)$ TO SECOND SYSTEM ~ 96 |
| 002 | $(D_5, D_6)$ | TIME 1 - MATCH $D_5$ TO $L_{10}$ AND $L_{11}$ ~ 102 |
| | | TIME 2 - SEND DATA STRUCTURE $(L_{10}, L_{11}, D_6)$ TO FIRST SYSTEM ~ 103 |
| | | TIME 3 - RECEIVE DATA STRUCTURE $(L_{10}, L_{11}, D_7)$ FROM FIRST SYSTEM ~ 104 |
| | | TIME 4 - SEND DATA STRUCTURE $(D_5, D_7)$ TO INITIALIZING DEVICE ~ 105 |
| | | TIME 4 - SEND DATA STRUCTURE $(L_{10}, L_{11}, D_5)$ TO REPORT TABLE ~ 106 |

Fig. 2

SOFTWARE SYSTEM
CONFIGURATION TABLE                              ← 275

| SOFTWARE SYSTEM | CLIENTS | ADDRESS |
|---|---|---|
| Software System 1 Accounting | Client 1 | Address 1 |
|  | Client 2 | Address 2 |
|  | Client 5 | Midware Address |
|  | Client 8 | Midware Address |
|  |  |  |
|  | Client (n) | Address (n) |
| Software System 2 Pharmacy | Client 2 | Address 2 |
|  | Client 4 | Address 4 |
|  | Client 9 | Midware Address |
|  |  |  |
|  | Client (n) | Address (n) |
| Software System 3 Nursing | Client 3 | Address 3 |
|  | Client 6 | Address 6 |
|  | Client 8 | Midware Address |
|  |  |  |
|  | Client (n) | Address (n) |
|  |  |  |
| Software System (n) |  |  |

TASK SPECIFIC
MAPPING TABLE

600

| ⎿605 | ⎿610 | ⎿615 | ⎿620 | ⎿625 |
|---|---|---|---|---|
| TASK | DATA STRUCTURE RCVD BY MIDWARE | SUBTASK | AUTHORIZED ADDRESS FOR PERFORMING SUBTASK | SELECTED ADDRESS |
| 001 | D1, D2, D3, D4 | Subtask 1 get fields S1, S2 | Sub-Client 5a | Sub-Client 5a |
| | | | Sub-Client 5b | |
| | | Subtask 2 get field S3, S4 | Sub-Client 5a | Sub-Client 5b |
| | | | Sub-Client 5b | |
| | | | Sub-Client 5c | |
| | | Subtask 3 match D3 to L1 | Internal Table | Internal Table |
| 002 | D5, D6 | Subtask 1 match D5 to L10 and L11 | External Table | External Table |
| | | Subtask 2 Get Fields L10, L11, D7 | Software System 35c | Software System 35c |
| 003 | D10, D11 | Subtask 1 Communicate D10 | Sub-Client 9a | Sub-Client 9a |
| | | Subtask 2 Communicate D11 | Sub-Client 9b | Sub-Client 9b |
| 004 | D15, D20 | Subtask 1 Get Fields L15, L20 | Sub-Client 5a | Sub-Client 5a |
| | | | Sub-Client 9a | |
| | | Subtask 2 Communicate D15 | Sub-Client 5b | Sub-Client 5b |
| | | | | |
| Task (n) | | | | |

Fig. 11

TRANSLATION TABLE

| TASK | RESPOND TO SYSTEM ⟵715 | SYSTEM TYPE ⟵720 | SOFT-WARE SYSTEM FIELDS ⟵725 | WHICH SUB-CLIENT / SYSTEM ⟵730 | RECEIVED RESPONSE ⟵735 | ERROR | ERROR HANDLING ⟵750 |
|---|---|---|---|---|---|---|---|
| 001 | | | | | | | |
| 002 | | | | | | | |
| 003 | | | | | | | |
| 004 | | | | | | | |
| 005 | | | | | | | |
| (n) | | | | | | | |

Fig. 12a

TRANSLATION TABLE
TASK 1

| TASK | RESPOND TO | SYSTEM TYPE | FIELDS | WHICH SUB-CLIENT / SYSTEM | RECEIVED RESPONSE | ERROR | ERROR HANDLING |
|---|---|---|---|---|---|---|---|
| 001 | Report Table | Table | D1 | n/a | | | |
| | | | D2 | n/a | | | |
| | | | Sub-Client 5a | n/a | | | |
| | Report Table | Table | D2 | n/a | | | |
| | | | D4 | n/a | | | |
| | | | Sub-Client 5b | n/a | | | |
| | Pharmacy | 3270 Emul | S1 | Sub-Client 5a | Sub-Client 5a y/n | error 1 | error handler 1 |
| | | | S2 | Sub-Client 5a | Sub-Client 5b y/n | error 2 | error handler 2 |
| | | | S3 | Sub-Client 5b | | error 3 | error handler 3 |
| | | | S4 | Sub-Client 5b | | error 4 | error handler 4 |
| | Accounting | ODBC | L1 | n/a | Sub-Client 5a y/n | error 5 | error handler 5 |
| | | | | | Sub-Client 5b y/n | error 6 | error handler 6 |
| | | | S2 | Sub-Client 5a | | error 7 | error handler 7 |
| | | | S4 | Sub-Client 5b | | error 8 | error handler 8 |
| | | | | | | error 9 | error handler 9 |

Fig. 12b

TRANSLATION TABLE
TASK 2

| TASK | RESPOND TO | SYSTEM TYPE | FIELDS | WHICH SUB-CLIENT / SYSTEM | RECEIVED RESPONSE | ERROR | ERROR HANDLING |
|---|---|---|---|---|---|---|---|
| 002 | Sub-Client 8a | Mobile | D5 | n/a | Nursing | error 20 | error handler 20 |
|  |  |  | D7 | Nursing | y/n | error 21 | error handler 21 |
|  | Report Table |  | L10 | n/a |  |  |  |
|  |  |  | L11 | n/a |  |  |  |
|  |  |  | D5 | n/a |  |  |  |

REPORT TABLE

| REPORT — 1010 | Report Field 1 Sub-Client Addr. — 1020 | Report Field 2 Time/Date — 1030 | Report Field 3 Patient — 1040 | ... | Report Field n — 1050 |
|---|---|---|---|---|---|
| Report 1 - Administer blood test | Sub-Client 5a | 8:30 am 3/1/98 | John Doe | | |
| | Sub-Client 5c | 9:00 am 8:14 am 3/1/98 | Jane Doe | | |
| | Sub-Client 9a | 10:27 am 3/2/98 | John Smit | | |
| | Sub-Client 8a | 6:30 pm 3/3/98 | Jane Smith | | |
| | | | | | |
| | | | | | |

| REPORT | Report Field 1 | Report Field 2 | Report Field 3 | ... | Report Field n |
|---|---|---|---|---|---|
| Report 2 | | | | | |
| | | | | | |
| | | | | | |
| | | | | | |

1000 (both tables)

Fig. 14

METHOD AND APPARATUS FOR INTERGRATING WIRELESS AND NON-WIRELESS DEVICES INTO AN ENTERPRISE COMPUTER NETWORK USING AN INTERFACING MIDWARE SERVER

CROSS REFERENCE TO RELATED APPLICATIONS

This applications is a related to U.S. patent application titled METHOD AND APPARATUS FOR TRACKING TRANSACTIONS IN AN ENTERPRISE COMPUTER NETWORK filed on the same date as the present application.

TECHNICAL FIELD

The present invention relates to the field of information exchange and retrieval in an enterprise computer network having a plurality of heterogenous software systems and a plurality of clients communicating with one another. More particularly, the present invention relates to the integration of a midware into the enterprise computer network for interfacing clients represented by a plurality of subclients with the software systems.

BACKGROUND OF THE INVENTION

In today's economy companies are frequently turning to software solutions to help integrate and streamline business processes and lower overall operational costs. For example, a typical business may include a variety of organizations such as accounting, purchasing, sales, warehousing, human resources, etc. The specialized needs of each organization leads to each organization using their own software system designed to handle the functions and tasks to be performed. For example, accounting may utilize a special financial software system which allows for convenient entry of a company's assets and liabilities while sales may utilize a different software system which allows for easy order entry and tracking.

Although each organization performs different functions it is, of course, necessary that the organizations exchange and retrieve information with one another on a timely basis. For instance, once sales has received a signed purchase agreement from a customer indicating that the customer has committed to purchasing a given number of products, the sales department must immediately inform the accounting department of the transaction such that the transaction may properly be logged in the accounting records. To communicate this information it is possible for an individual in the sales department to send a paper or electronic form to the accounting department indicating the transaction which has taken place. Unfortunately, such procedures are often cumbersome and result in errors. For such reasons, enterprise wide software management systems have been developed.

Enterprise wide software management systems integrate both heterogenous and homogeneous software systems such that information may be exchanged, retrieved and updated among many systems and clients in real time. For instance, in the example above, an enterprise wide software management system would provide the appropriate connectivity to allow the accounting records to be automatically updated upon an individual from the sales department entering information related to the new purchase order. Thus, there is no need for the sales department to track and forward this information consciously to the other appropriate organizations in the company thereby minimizing overhead and reducing the possibility of introducing errors into the information to be shared.

In order to provide the necessary connectivity among different software systems and other clients in a particular business or corporation, specialized consultants or other information services individuals are often contracted by the business entity to configure a given enterprise wide software management system to meet the precise needs of the company. Configuring an enterprise wide software management system to a particular companies needs may often take several months to several years to complete depending on the size of the project at hand.

As companies and businesses continue to grow and expand, a recent trend has been to integrate wireless communications into a company's network infrastructure to help further optimize operations. For instance, wireless communication devices may take the form of wireless bar code readers which are used in a company's warehouse to help track inventory, wireless pen computing devices which may be used by individuals on a manufacturing floor to log problems or request replacement parts, and wireless arm mounted terminals which may be used by warehouse pickers to receive orders for replacement parts in real time so that the order may be filled immediately. As the price of these and other wireless computing devices continues to drop, the use of such devices by a company to increase productivity and efficiency continues to grow.

In companies having an enterprise wide software management system it is desirous to integrate wireless computing devices into to the enterprise wide system in order to utilize the wireless computing devices to their maximum potential. For instance, prior to the introduction of wireless computing devices into a company's manufacturing facility, an enterprise wide software management system may have been configured to send all requests for replacement parts to a central computer near a company's stockroom of replacement parts. Pickers who physically fill the requests would periodically check and retrieve new orders from the computer system or inform the requester if parts were currently unavailable. Upon providing each picker with a wireless arm mounted terminals, however, it would be desirous for replacement part requests to be routed directly to the appropriate picker's wireless terminal by the enterprise wide software management system. Further, it would be desirous for the picker to be able to respond directly back to the enterprise wide software management system as to whether the order has been filled or if the parts were unavailable and to automatically update the appropriate software systems in the company of the picker's transactions.

While it may be possible to reconfigure the enterprise wide software management system to provide the appropriate connectivity between each wireless terminal and the other software systems in a company, such reconfiguration would be extremely costly and time consuming. For instance, during reconfiguration, the enterprise wide software management system may need to be taken off line for several days or months so that the system can be updated with appropriate routing commands for each new wireless terminal. Further, such difficulties of updating and reconfiguring the enterprise wide software management system would occur each time additional wired and/or wireless terminals was to be fully integrated into the company's network infrastructure.

Therefore, what is needed is a method and apparatus of integrating wired and wireless devices into an existing computer network running an enterprise wide software management system which overcomes the difficulties described above and others.

SUMMARY OF THE INVENTION

The present invention provides a method and apparatus for integrating one or more clients represented by a plurality of subclients into an existing enterprise wide software management system. Each subclient may take the form of wireless mobile terminals or other devices which may be introduced and removed from the enterprise computer network on a regular basis. Integration of the subclients into the enterprise wide software management system is accomplished by way of midware which serves to provide appropriate transformation and routing of communication between the subclients and one or more software systems within the enterprise wide software management system. Thus, the midware allows the enterprise wide software management system may communicate with the subclients without being reconfigured to communicate specifically with each individual subclient.

The midware is configured to appropriately transform, manipulate, and route communications originating from one or more software systems to one or more subclients. Further, the midware is configured to appropriately transform, manipulate, and route communications originating from one or more subclients to one or more software systems. In transforming communications from a data structure of a receiving device to a data structure of a destination device, the midware is also configured to actively obtain any incomplete or deficient information. For example, the midware may query additional devices for such information or, if available, provide the information from the midware's own internal tables.

In order to determine the appropriate routing protocol for a given communication, the midware maintains a set of tables. The tables define for the midware the appropriate action which needs to be taken to respond to a particular task. Further, the tables keep track of which subclients are currently available to perform each task/subtask. Availability of a subclient is determined based on whether the subclient is currently registered with the midware. If more than one subclient is available, the tables further include a priority scheme to determine which of the available subclients should be selected to perform the task at hand.

With respect to communications originating from the software systems, the operations performed by the midware typically takes one or two forms. The first type of operation is one in which the midware forwards a communication to a particular client. For example, if the midware receives communication from a software system directed to a first client, the midware tables may indicate to the midware that first client is represented by first and second subclients and that half of the communication should be forwarded to the first subclient and the other half of the communication should be forwarded to the second subclient. Prior to routing such information, the midware would also reconfigure the communications to an appropriate data structure for the first and second subclients. The second type of operation performed by the midware involves a situation where the midware is to provide a response to a communication it received on behalf of a client represented by the midware. As the client is actually represented by subclients, the midware forwards the appropriate instructions to one or more subclients, waits for a response from each of the subclients, performs other appropriate operations to provide information in a particular format, and then forwards a single collective response to one or more assigned destination devices. For instance, the midware may determine that a particular task received by the midware should be routed to three subclient following which the midware should obtain a response from each of the subclients and forward a collective response to the originating software system and one other software system. In the event one or more of the subclients do not respond to a request for information, the midware is further configured to query the non-responding subclients for the desired information. In responding to a request it is also possible that the midware obtains certain response data from other sources. For example, if the current time and date was to be included in a response, such information may be provided by the midware itself.

With respect to communications originating from the subclients, the types of operations performed by the midware also typically takes one or two forms. The first type of operation is one in which the midware transforms the communication to an appropriate data structure and forwards a subclient's communication without the need to retrieve additional information. For instance, the subclient's task may involve forwarding the information provided in its entirety to two different software systems. The second type of operation is one in which prior to forwarding the subclient's communication, the midware needs to retrieve additional information. For instance, the subclient's task may enlist the midware to query two other subclients for information which is then collectively routed to one or more software systems.

In addition to routing communications, the midware is also configured to track certain predefined transactions carried on by subclients and generate reports based on the transactions which have taken place. More particularly, during the routing of communications through the midware, the midware continually monitors for the predefined transactions and, if found, automatically updates an appropriate table with such information such that a report of all such transactions may ultimately be recovered.

The midware may also be configured to serve as the primary processing power and memory for one or more subclients. More particularly, in order to allow for "thin" mobile devices, the midware may perform a large portion of the processing tasks for a given mobile device and transmit communications to the mobile devices which allow the mobile devices to display the results. For instance, the midware may include a bar code parse circuit which parses decoded bar code data forwarded by a mobile device. Thus, mobile devices having bar code readers would not need to include the additional barcode parse circuitry within the device itself. By shifting these and other conventional processing tasks to the midware, the mobile device may be designed in a more cost effective manner.

According to one aspect of the present invention, a midware server for use in an enterprise computer network having an enterprise management system and a plurality of clients communicatively coupled to the enterprise management system is provided. The midware server includes a network interface for communicatively coupling the enterprise management system to at least one of the plurality of clients functionally represented by a plurality of subclients, and a task processing circuitry for converting at least a portion of communications received according to a first data structure compatible with one of the enterprise management system and a first of the plurality of subclients to a second data structure different than the first data structure compatible with the other of the enterprise management system and the first of the plurality of subclients.

According to another aspect of the present invention a midware server for use in an enterprise computer network is provided. The enterprise computer network includes an enterprise management system for communicating with a plurality of clients within an enterprise network. The midware server includes a first communication means operatively coupling the midware server to the enterprise management system; a second communication means operatively coupling the midware server to at least one client of the plurality of clients, the at least one client functionally being represented by a plurality of subclients coupled to the midware server via the second communication means, and means for mapping, according to a predefined criteria, all or part of a communication received from the enterprise management system and directed to the at least one client to at least one of the plurality of subclients functionally representing the at least one client.

According to another aspect of the present invention, a midware server for use in an enterprise computer network is provided. The enterprise computer network includes an enterprise management system for communicating with a plurality of clients within an enterprise network. The midware server includes a first communication means operatively coupling the midware server to the enterprise management system; a second communication means operatively coupling the midware server to at least one client of the plurality of clients, each of the at least one client comprising a plurality of subclients functionally representing the respective at least one client, and means for mapping, according to a predefined criteria, all or part of individual communications received from at least one of the plurality of subclients to the enterprise management system.

According to still another aspect of the present invention, a midware server for use in an enterprise computer network is provided. The enterprise computer network includes an enterprise management system for communicating with a plurality of clients within an enterprise network. The midware server includes a first communication means operatively coupling the midware server to the enterprise management system; a second communication means operatively coupling the midware server to at least one client of the plurality of clients, the at least one client functionally being represented by a plurality of subclients coupled to the midware server via the second communication means, and means for mapping, according to a predefined criteria, all or part of a task command received from the enterprise management system and directed to the at least one client as subtasks to at least one of the plurality of subclients functionally representing the at least one client, the task command representing a task to be carried out by the at least one client and the subtasks representing at least part of the task.

According to yet another aspect of the present invention a mobile terminal for use in an enterprise computer network having a midware for communicatively interfacing an enterprise management system with one or more clients each represented by a plurality of subclients is provided. The mobile terminal includes a portable housing, a processor disposed in the housing, and means for transmitting and receiving wireless communications coupled to the processor, wherein the mobile terminal registers with the midware server in order to transmit and receive communication with the enterprise management system.

According to still yet another aspect of the present invention an enterprise network having an enterprise management system and a plurality of subclients representing one or more clients communicating with the enterprise management system through a midware is provided. A method includes the steps of receiving communications at the midware from one of the enterprise management system and a first of the plurality of subclients, converting at least a portion of the communications received into a data structure compatible with the other of the enterprise management system and the first of the plurality of subclients, and transmitting the at least a portion of the communications to the other of the enterprise management system and the first of the plurality of subclients according to the data structure.

According to still yet another aspect of the present invention In an enterprise network having an enterprise management system and a plurality of subclients representing a client communicating with the enterprise management system through a midware is provided. A method includes the steps of transmitting by the enterprise network communication destined for the client, receiving the communication by the midware, converting at least a portion of the communication to a first format compatible with a first of the plurality of subclients and another portion of the communication to a second format compatible with a second of the plurality of subclients, and transmitting the at least a portion of the communication to the first of the plurality of subclients in the first format and the at least another portion of the communication to the second of the plurality of subclients in the second format.

To the accomplishment of the foregoing and related ends, the invention then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIG. 2 is a table depicting two exemplary tasks carried out by the midware in accordance with the present invention;

FIG. 6 is a software system configuration table maintained by the enterprise system in accordance with the present invention;

FIG. 11 is a task table maintained by the midware in accordance with the present invention;

FIG. 12a is a translation table maintained by the midware in accordance with the present invention;

FIG. 12b is one task of the translation table originated by a software system in accordance with the present invention;

FIG. 12c is one task of the translation table originated by a subclient in accordance with the present intention;

FIG. 14 is a report table maintained by the midware in accordance with the present invention;

DETAILED DESCRIPTION OF THE INVENTION

Figure 1:
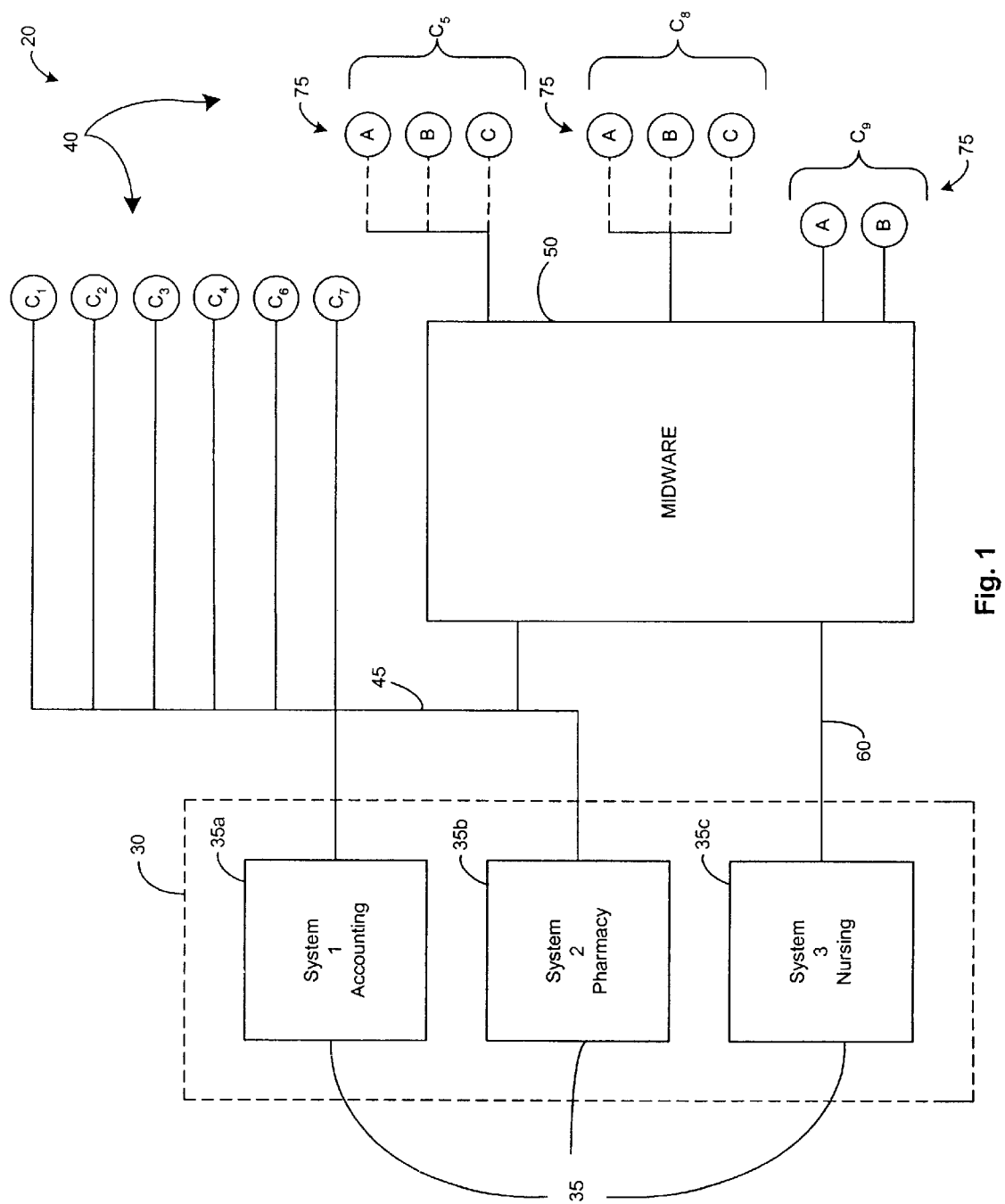
FIG. 1 is a block diagram overview of an enterprise computer network having a midware in accordance with the present invention.

The present invention will now be described with reference to the drawings in which like reference numerals are used to refer to like elements throughout.

Turning now to FIG. 1, an enterprise computer network 20 is shown in which an enterprise wide software management system 30 (hereinafter referred to as enterprise system 30) is installed for integrating various software systems 35 and clients 40. The enterprise wide software management system 30 may, for example, be a version of SAP, Bann, Oracle, PeopleSoft, or other network integration system as is generally known in the art. In the present embodiment, the network 20 is shown to include three heterogeneous software systems 35 operating in a hospital environment. In particular, system 35a represents a first software system operating in the hospital's accounting department, system 35b represents a second software system operating in the hospital's pharmacy department, and system 35c represents a third software system operating in the hospital's nursing department. Each software system 35 is configured to interface with a respective set of clients 40 in order to communicate and retrieve information. It is possible for two or more different software systems 35 to be configured to communicate with one or more of the same clients 40. Further, the enterprise system 30 enables communications originating in one software system 35 to be shared with another software systems 35 where the communications may be transmitted to the clients 40 of the other software system 35 in accordance with instructions preconfigured into the enterprise system 30. It will be appreciated that while the present embodiment depicts three software systems 35 operating in a hospital environment, the present invention is suitable for use with any number or software systems operating in any business, government, or other environment including, for example, technology, retail, finance, warehousing, transportation, perishable goods, etc.

In the present embodiment, each software system 35 is preconfigured to communicate with one or more of the clients 40 represented by c1–c9. With respect to each client 40 with which a software system 35 is configured to communicate, the software system 35 further includes prestored information related to the data structure or format in which communication is to be exchanged with each affiliated client 40. For example, client c1 may expect to receive information in a format defined by a first data structure which is different than a data structure in which client c2 expects to receive data. Thus, the software system 35 maintains information related to the data structure of each device with which the software system 35 intends to communicate.

Each software system 35 of an enterprise system 20 is preconfigured to communicate with specified clients 40 using a predetermined format or data structure. An appropriate data structure is typically selected by the respective software system 35 for communication with a client 40 from preconfigured standards. For instance, the software system 35 may be designed to communicate with desktop computers connected to an ethernet LAN using one preconfigured standard. However, upon introducing clients 40 to the enterprise system 20 for which the software system 35 does not have a preconfigured standard for communication, the software system 35 would need to be reconfigured to communicate with such clients. Thus, for example, the introduction of wireless mobile devices to the enterprise system 20 often involve communicating using a specialized protocol which takes into account the mobile nature of such devices. As discussed in the background section, such reconfiguration of the software systems 35 is often time consuming and expensive. By including a midware server 50 (hereinafter referred to as midware 50), the present invention provides an efficient manner in which devices may communicate with the software systems 35 in a non-conventional manner. Further, the midware server 50 provides an efficient manner to integrate multiple devices into an existing enterprise system 20. In particular, the midware 50 allows for such integration of additional devices by representing a client 40 with one or more subclients 75 which are transparent to the enterprise system 30 and performing the steps needed to allow communication to take place. Thus, for example, a given software system 35 may be interfaced with two or more subclients 75 through the midware 50 even though the software system 35 is preconfigured to communicate with only one client 40. Similarly, with respect to communications originating from the subclients 75, the midware 50 reformats the communication into an appropriate format for routing to the appropriate software system 35.

Advantages of the midware 50 may be seen with respect to the hospital environment depicted in FIG. 1. For example, the pharmacy software system 35b may have originally been configured (at the time of installation) to communicate with client c1 which represents a computer system in which doctors input authorized prescribed drugs for each patient, and client c5 which originally represented a single computer system in which nurses entered re-fill order requests. In order to provide faster service, the hospital later decides to provide each nurse with a wireless pen base computer in which the nurses automatically enter re-fill orders as they visit each patient and determine such a need exists. Rather than reconfiguring the software systems 35 to communicate with each individual nurse via their respective wireless pen based computer, the present invention allows the midware 50 to effectively represent all of the wireless pen base computers as a single client to the software systems 35. Thus, each software system 35 continues to believe it is communicating with a single client c5, however, the midware 50 is programmed to automatically convert communications to appropriate data structures and route communications directed to client c5 to one or more of the appropriate subclients 75 which collectively represent client c5. As additional wireless pen based computers or other devices are added or removed from the hospital for performing the re-fill order task, these devices may be introduced and removed through the midware 50 while remaining transparent to the software systems 35.

Similarly, in the retail industry, an enterprise system 30 may have originally been configured to receive all inventory data from a single computer of a store. However, as wireless bar code reading devices become increasingly popular, inventory is often taken by a several individuals operating such devices on the retail floor. As such, use of a midware to interface the existing enterprise system with such additional devices provides a cost effective and efficient way of providing such integration.

Referring now to FIG. 2, a table 80 is shown exemplifying the manner in which the midware 50 may be configured to perform certain tasks. As will be discussed in more detail below, a task is initiated when an initiating device (whether it is a software system 35, client 40, or subclient 75) transmits information to a client 40 which is represented by the midware 50. The midware 50, receives the communication and based on its content performs a particular task as represented by column 81. More particularly, the communication includes a task request and an appropriate data structure associated with the task as represented in column 82. Alternatively, the communication may include just the task to be performed and the receiving, which in this case is the midware 50, may be preconfigured handle the task according to known data structure. In the present example, the data structure associated with task 1 is represented by D1, D2, D3, D4. For instance, if task 1 represents a request by the pharmacy software system 35b to receive data related to certain drugs administered by a particular doctor then D1 may represent the name of a first drug, D2 may represent the name of a second drug, D3 may represent the name of the doctor, and D4 may represent the time frame of interest.

In order to perform task 1, the midware 50 is shown to perform a series of preconfigured operations as depicted in column 83. Each operation is indexed by a unit of time which represents the sequence in which the individual operations are performed. Thus, for example, each of the operations indexed by "Time 1" is performed by the midware 50 substantially simultaneously, while those operations indexed by "Time 2" occur at some time after "Time 1" etc. In order to perform task 1, the midware 50 is shown to perform a series of subtasks. More particularly, at step 85, the midware is shown to select a sub-client to perform subtask 1 which is to retrieve information related to drug D1. As will be discussed in more detail below, selection of a subclient to perform a particular subtask is handled through a task specific mapping table 600 (FIG. 11) stored in the midware 50. In this particular example, the midware 50 is shown to have selected subclient 5a to perform subtask 1.

Once the subclient has been selected, the midware 50 in step 86 sends to subclient 5a the information needed to perform its subtask according to the known data structure for subclient 5a. For instance, in the present example, subclient 5a is a pen based computer assigned to the doctor at a first hospital and is configured to receive data in the form of a drug name (e.g. D1) and time period (e.g. D4) for which information is sought. Next, in step 87, the midware 50 receives a data structure S1, and S2 from subclient 5a. For example, S1 may represent the name of the drug for which information was requested and S2 may represent the amount of the drug administered during the time period specified in D4.

Similar to that discussed above with respect to step 85, the midware 50 in step 88 selects subclient 5b to perform subtask 2 which in this case is to retrieve information related to drug D2. In the present example, subclient 5b represents a different pen based computer assigned to the doctor at a different hospital. In response to the data structure sent to the subclient 5b in step 89, the midware 50 is shown to receive data structure S3 and S4 wherein S3 in this example represents the name of the drug D2 and S4 represents the amount of the drug D2 that was administered during the time period specified in D4.

Referring to step 92, the midware 50 is also shown to match the data structure D3 with data structure L1 in order to conform with one or more data structures of devices which are to be responded to in task 1. For instance, in the present example D3 represents the doctor's name by way of a series of alphanumeric characters. However, the data structure of certain systems with which the midware 50 is configured to respond may only accepts social security numbers and not actual names. As such, the midware 50 accesses a table which may be either external or internal to the midware 50 which allows the midware to retrieve the doctor's social security number L1 based on the name provided.

In steps 93–96 the midware is shown to respond to various places according to the data structure shown. For instance, in steps 93 and 94 the midware 50 is shown to send a response data structure to a report table 1000 (FIG. 14) which stores the information in a report format as is discussed in more detail below. In step 95 and 96 the midware 50 is shown to send a predefined data structure to the initiating pharmaceutical software system 35b and to a second software system (e.g. accounting software system 35a).

Continuing to refer to FIG. 2, a call for the midware 50 to complete task 2 is shown to involve the initiating system providing the midware 50 with data structure D5 and D6. For instance, task 2 in the present example is a request by subclient 8a to retrieve a particular patient's blood pressure. Correspondingly, D5 represents the patient's name and D6 represents a field indicating that blood pressure data is desired. Referring again to the midware operation column 83, in step 102 the midware 50 is shown to match data structure D5 with data structures L10 and L11. As discussed above, the matching allows the midware 50 to obtain data in an appropriate format for communicating with other devices or places. In this example, the patient's name D5 is matched with the patient's room number L10 and bed number L11. Thus, the midware 50 is able to communicate with those devices having a data structure which represents a patient by a room and bed number rather than the patient's name. In order to perform the matching, the midware 50 may access a table stored internally or an external table.

Next, in step 103 the midware 50 transmits a data structure having fields L10, L11 and D6 to a first system which in this case is the nursing software system 35c. In response, the midware 50 receives in step 104 a data structure from the nursing software system 35c which includes field D7 which represent the patient's blood pressure. Finally, in steps 105 and 106 the midware 50 sends the data in accordance with a corresponding data structure shown in the table to both the initiating device (subclient 8a) and to the report table 1000 for logging.

While the above examples serve to exemplify some of the functions of the midware 50, it will be appreciated that midware 50 is able to perform a variety of other functions described herein and the example shown in FIG. 2 is not meant to encompass the full operational scope of the midware.

Referring now to FIGS. 3a–3f, a summary of several midware routing protocols is shown in which the midware 50 interfaces two software systems 35a, 35b with two subclients 75a, 75b. In the present example, the two subclients 75a, 75b represent a single client X. As discussed above, however, that the midware 50 can of course interface multiple clients 40 each represented by a plurality of subclients 75. The procedure for determining how information is routed by the system 35 and by the midware 50 is discussed in more detail below. For the present example, however, it is assumed that each system 35a, 35b is configured to transmit information to client X through the midware 50. Additionally, the midware 50 is configured to route some or all of the information destined for client X to one or both subclients 75a, 75b depending on the task and subtasks at hand.

Figure 3A:
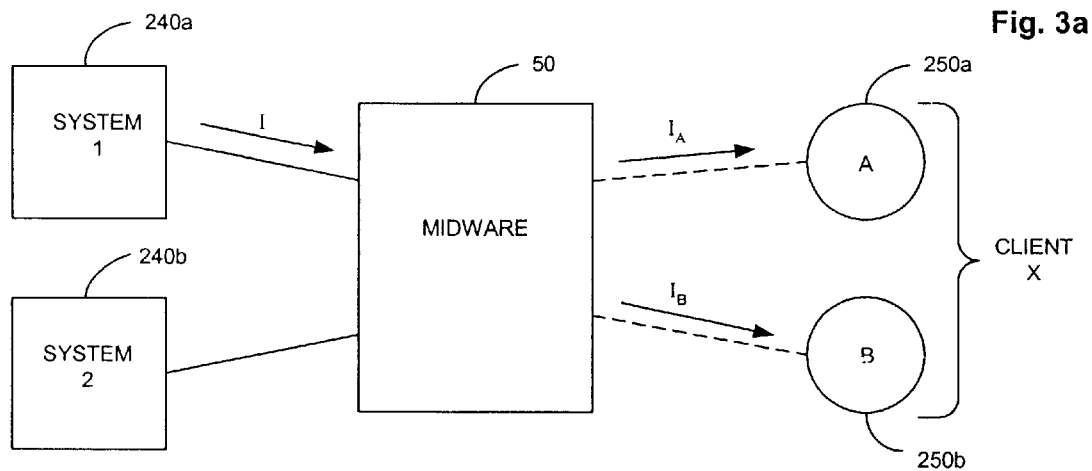
FIG. 3a is a diagrammatic representation of the midware routing communication from a single software system to two subclients in accordance with the present invention.

Beginning with FIG. 3a, there is shown a scenario where a single system 35a transmits information "I" to client X which is handled by the midware 50. Upon receiving the information "I" the midware 50 determines that the task at hand involves communicating a portion of the information "I" to subclient 75a and a portion of the information "I" to subclient 75b. As such, the midware 50 routes a first portion of the information to subclient 75a as depicted by "Ia" and a second portion of the information to subclient 75b as depicted by "Ib". For example, the nursing software system 35c may be transmitting information to a computer system (e.g. client X) on the third floor of a hospital to administer drugs to patient y and patient z. The third floor computer system is, however, now represented by the midware 50 which receives the communication from the nursing software system 35c and performs the necessary conversions to forward information related to patient y (e.g. Ia) to subclient 75a and information related to patient z (e.g. Ib) to subclient 75b.

Figure 3B:
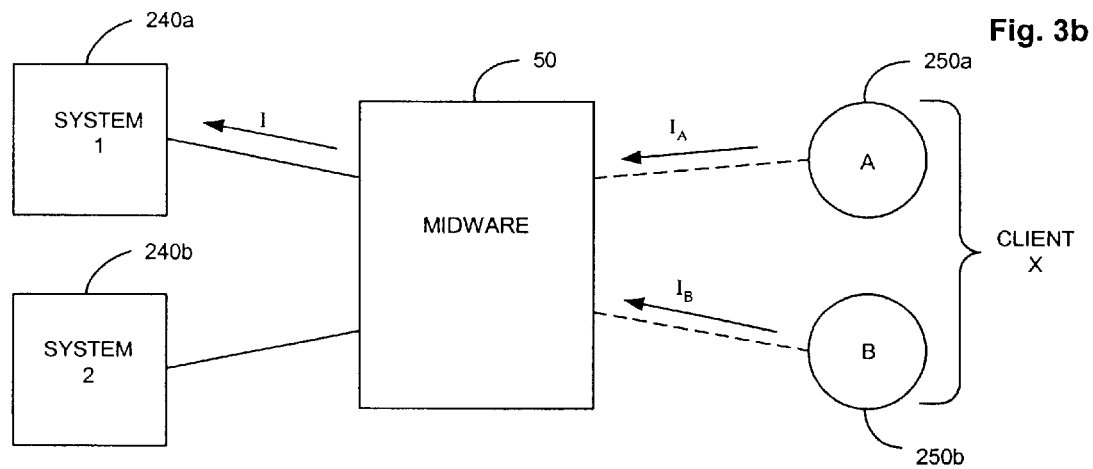
FIG. 3b is a diagrammatic representation of the midware routing communication from two subclients to a single software system in accordance with the present invention.

FIG. 3b represents a situation in which the midware 50 receives information "Ia" from subclient 75a and information "Ib" from subclient 75b for routing to system 35a. This situation may, for instance, arise following a request by the midware 50 for each subclient 75a, 75b to respond to a particular subtask. In FIG. 3b the midware 50 is shown to combine the data received from both subclients 75a, 75b and forward a single communication "I" to the system 35a having the combined data. It will be appreciated that the information "Ia" and "Ib" to be combined and forwarded to the system 35a may be received simultaneously or sequentially in time by the midware 50. Further, it is possible that if either one or both of the subclients 75a, 75b had failed to provide the midware 50 with the information to be forwarded to the system 35a within a predetermined period of time from when the midware 50 expected to receive the information, the midware 50 would have queried the non-responding subclient 75a, 75b for the missing information.

Figure 3C:
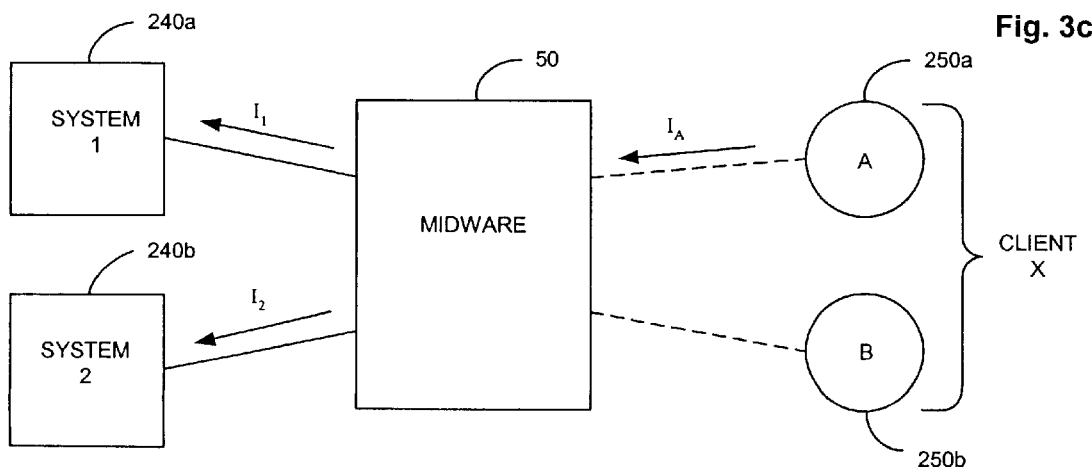
FIG. 3c is a diagrammatic representation of the midware routing communication from one subclient to two software systems in accordance with the present invention.

FIG. 3c represents a situation where a single subclient 75a transmits information "Ia" to the midware 50 which is then routed by the midware 50 to both system 35a and system 35b. As will be discussed in more detail below, the midware 50 may transmit all or part of the information "Ia" it receives from the subclient 75a to each system 35a, 35b as depicted by "I1" and "I2" respectively. Further, it will be appreciated, that the information contained in "I1" and "I2" may include additional information obtained by the midware 50 from other sources.

Figure 3D:
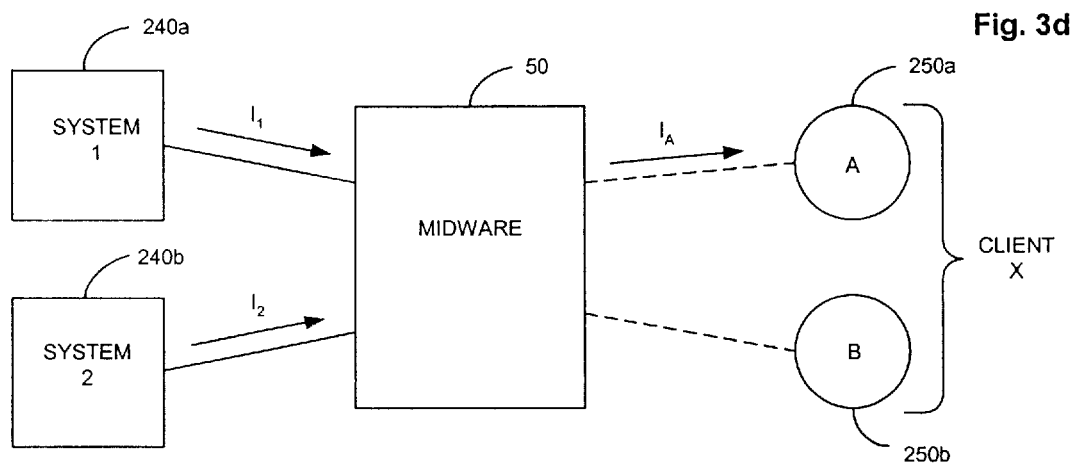
FIG. 3d is a diagrammatic representation of the midware routing communication from two software system to one subclient in accordance with the present invention.

FIG. 3d represents a situation where two systems 35a, 35b transmit information "I1" and "I2" to the midware 50 for routing to client X and in which the midware 50 combines the information and routes the combined information to subclient 75a. The information "Ia" routed to subclient 75a may include some or all of the combined information "I1" and "I2" received from the systems 35a, 35b and/or additional information obtained by the midware 50 from other sources.

Figure 3E:
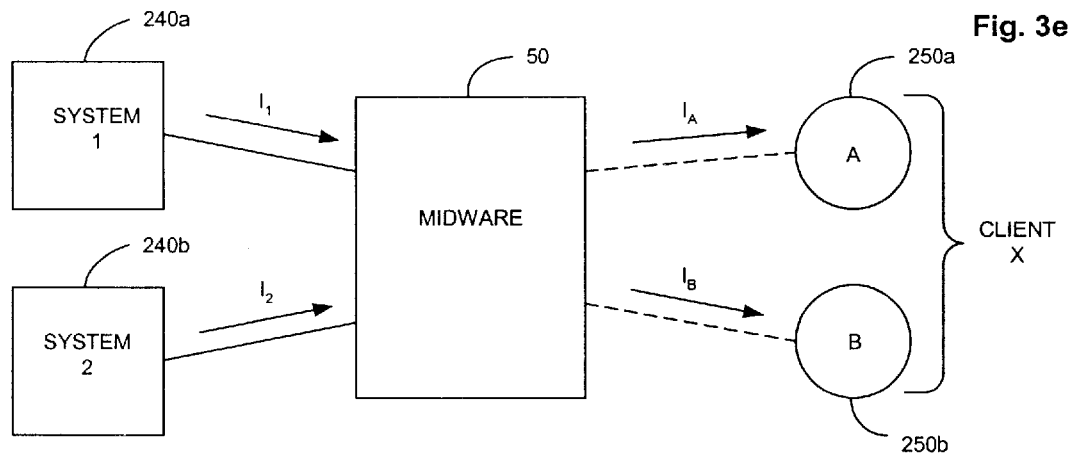
FIG. 3e is a diagrammatic representation of the midware routing communication from two software systems to two subclients in accordance with the present invention.

FIG. 3e represents a situation in which system 35a transmits information "I1" to the midware 50 at approximately the same time system 35b transmits information "I2" to the midware 50 and wherein the midware 50 routes a first portion "Ia" of the combined data to subclient 75a and a second portion "Ib" of the combined data to subclient 75b. As with previous examples, the portions "Ia" and "Ib" of the combined data to be routed to each subclient 75a, 75b by the midware 50 may each include the same information or may include different portions of the combined data as determined by the midware 50.

Figure 3F:
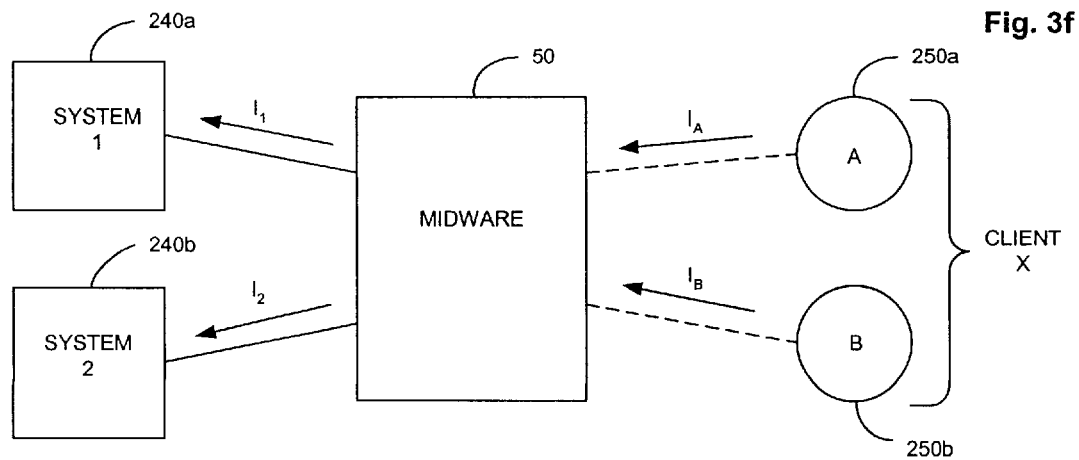
FIG. 3f is a diagrammatic representation of the midware routing communication from two subclients to two software systems in accordance with the present invention.

FIG. 3f represents a situation in which subclient 75a and subclient 75b each transmit information "Ia" and "Ib" to the midware 50 and in which the midware 50 routes some or all of the combined information to each system 35a, 35b. Similar to the example of FIG. 3b, it is possible that if the midware 50 does not receive information from both subclients 75a, 75b within a predetermined period of time, the midware 50 may be configured to query for the missing information prior to forwarding the information to the respective systems 35a, 35b.

It will be appreciated that FIGS. 3a–3f represent just a few examples of the possible routing protocols which the midware 50 is configured to handle. However, as can be seen from these examples, the midware 50 serves to interface subclients 75 with software systems 35 by virtue of assuming the identity of one or more clients from the perspective of the software systems 35. Thus, the software systems 35 which are configured to communicate with one client at a time are now able to effectively communicate with multiple clients at a time through the midware 50. As additional subclients 75 such as mobile terminals 98 are added to a network 20, the additional subclients 75 may be configured to communicate through the midware 50 thereby minimizing the amount of re-configuration needed to the enterprises system 30 to incorporate the new devices.

Referring again to FIG. 1, clients c1, c2, c3, c4, c6, and c7 each interface with software systems 35a, 35b, respectively, via a common physical network connection 45. The network connection 45 may, for instance, be an ethernet, token ring, local talk, or other known network connection. Clients c5, c8 and c9 interface with the software systems 35 via the midware server 50. In the present embodiment, systems 35a and 35b interface with the midware 50 via the network connection 45 while systems 35c is directly connected to the midware 50 via a direct physical network connection 60.

In the present embodiment, clients c1, c2, c3, c4, c6, and c7 each represent computer system located at various local and remote locations from the software systems 35. For instance, client c1–c4 may be located within the same building as one or more software systems 35, while clients c6 and c7 may be located at a regional offsite office, warehouse, or other facility. Clients c5, c8 and c9 may similarly be located local to or remote from software systems 35 and are each functionally represented by two or more subclients 75. More particularly, client c5 is shown to be represented by three wireless subclients 5a, 5b, and 5c, client c8 is shown to be represented by three wireless subclients 8a, 8b, and 8c and client 9 is shown to be represented by two subclients 9a, 9b which are each directly connected to the midware 50 via conventional network connections 37 and 38, respectively.

Figure 4:
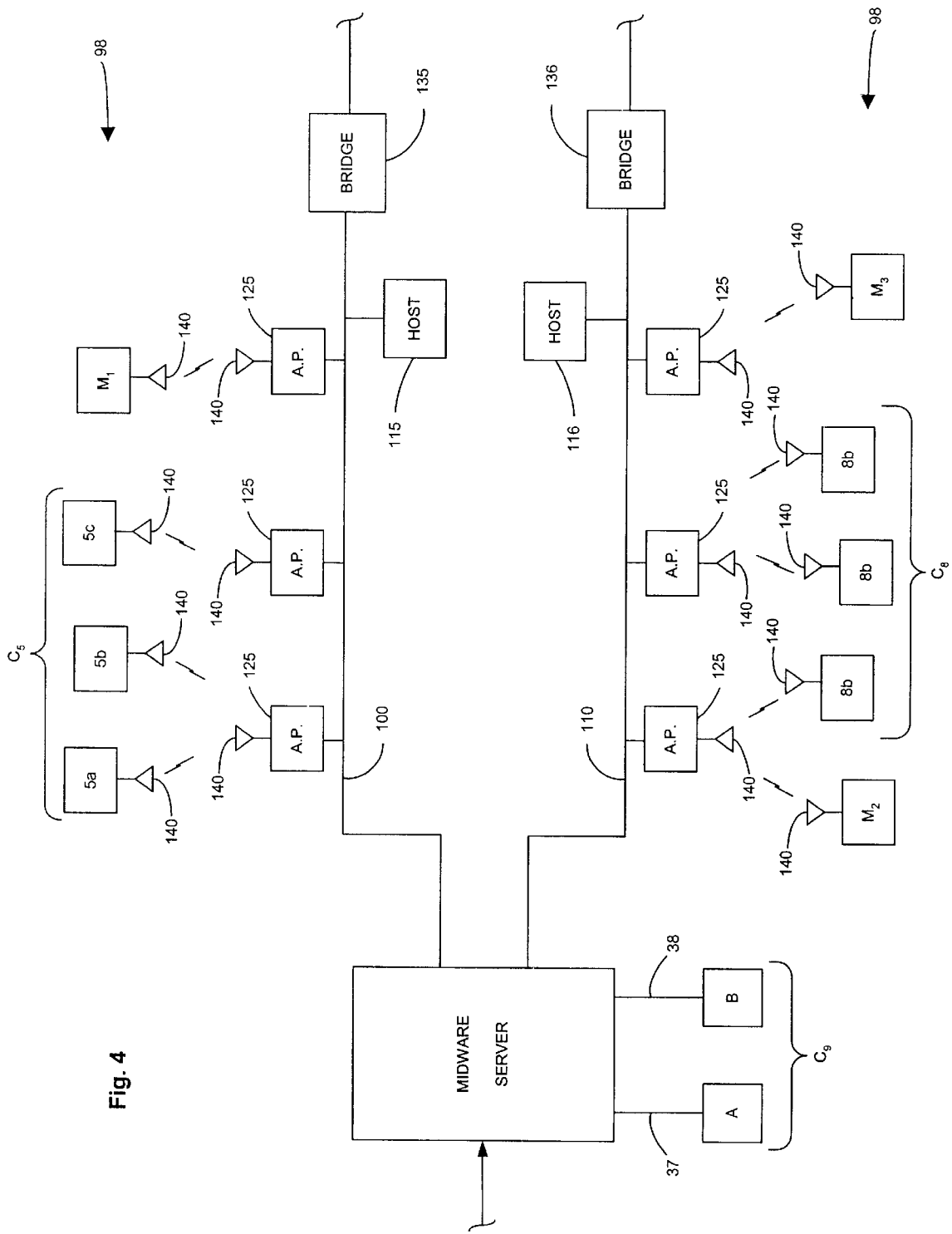
FIG. 4 is a detailed block diagram of an interface between the midware and subclients in accordance with the present invention.

Referring now to FIG. 4, the interface between the midware 50 and subclients 75 is shown in more detail. As shown, a plurality of mobile terminals 98 which include wireless subclients 5a–5c and 8a–8c are coupled to the midware 50 via a first and second LAN 100, 110 respectively. Each LAN 100, 110 includes a plurality of access points 125 for interfacing the mobile terminals 98 with one or more devices coupled to the LAN 100, 110. For instance, mobile terminals 98 may communicate via an access point 125 with the midware 50, host computers 115, 116, other mobile terminals 98 and/or with devices coupled to other LANs via bridge 135, 136. In order to allow for wireless transmission and receipt of data, each access point 125 and each mobile terminal 98 include an antenna 140. As is conventional, the type of antenna selected plays a significant factor in determining a particular device's communication cell coverage area. In the present embodiment, the antennas 140 are each omni directional antennas thereby providing for a generally spherical cell coverage. It will be appreciated, however, that directional, yagi and other types of antennas could alternatively be used to define a variety of cell coverage shapes and sizes.

In order to allow for transparent routing of information, each mobile terminal 98 registers with and communicates through a selected access point 125 in the mobile terminal's 98 cell coverage area. If the mobile terminal 98 roams out of cell coverage area of the access point 125 with which it is currently registered, the mobile terminal 98 attempts to register with a new access point 125 in order to maintain substantially fluid connectivity with the LAN 100, 110. Registration of a mobile terminal 98 with a new access point 125 triggers the new access point 125 to inform all other access points 125 on the particular LAN 100, 110 of the new registration thereby ensuring that only one access point 125 routes communication to and from the particular mobile terminal 98 at any given time. The access points 125 each maintain a table of those mobile terminals 98 currently registered therewith and monitor for communications destined to or received from such mobile terminals 98 in a conventional manner. Thus, devices attempting to communicate with a given mobile terminal 98 do not need to continually track the current location of the mobile terminal 98 since the access points 125 serve as a transparent interface for appropriately routing such information.

Figure 5:
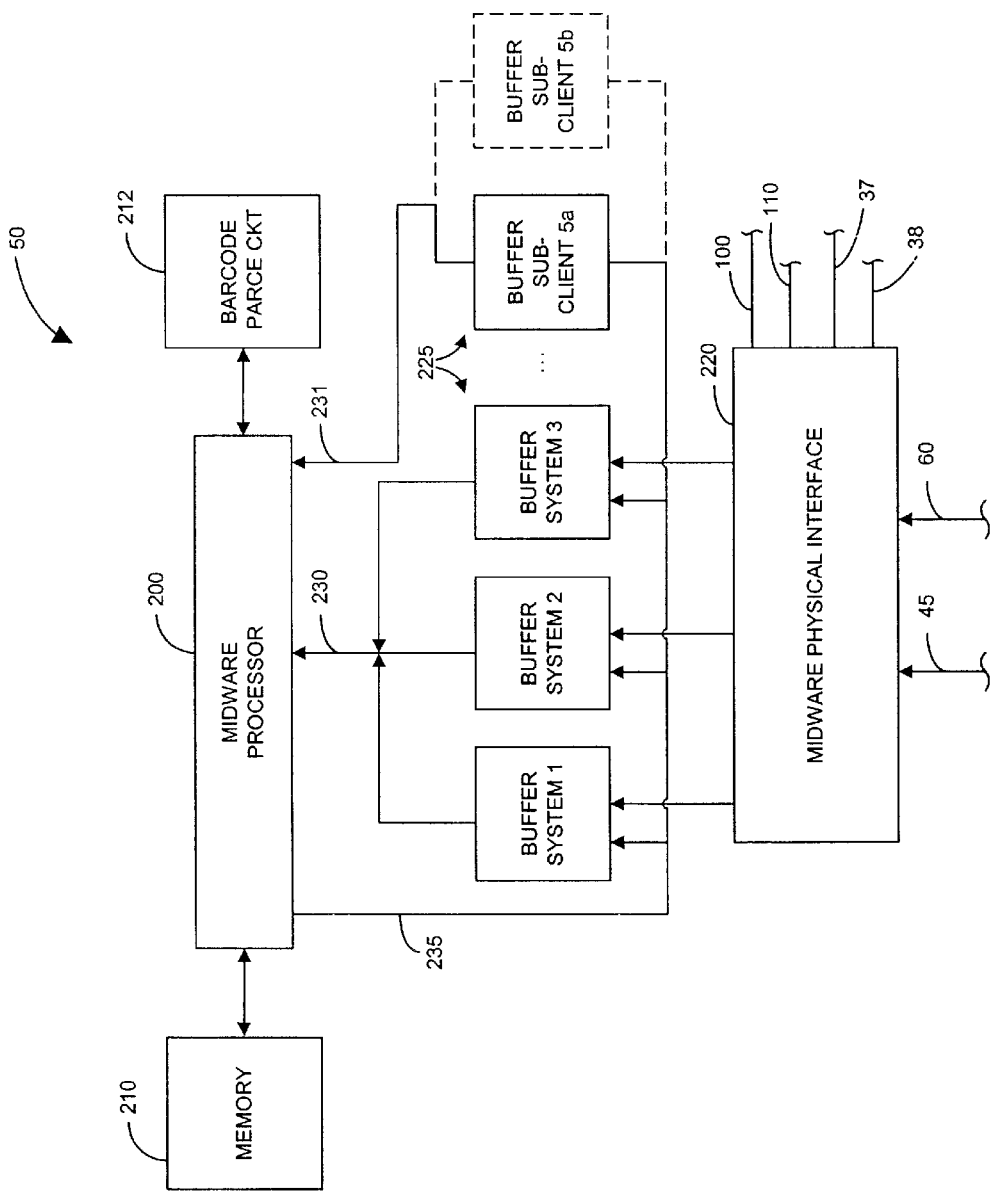
FIG. 5 is a block diagram of the hardware components of the midware in accordance with the present invention.

Referring now to FIG. 5, the internal hardware components of the midware 50 is shown in more detail. As shown, the midware 50 includes a midware processor 200 such as a 300 MHZ Intel Pentium II processor for carrying out the operations of the midware 50. A memory 210 is coupled to the processor 200 and stores data and executable code in order to perform the functions described herein. Also shown coupled to the processor 200 is a barcode parse circuit 212 which is discussed in more detail below. A conventional physical interface 220 provides interconnection of the midware 50 with the network backbone 45, direct physical network connection 60, 37, 38, and LANs 100, 110. The physical interface 220 couples to the processor 200 through a series of buffers 225. Each of the buffers 225 serves as a latch for storing task requests from the software systems 35 and subclients 75. In the present embodiment, the processor 200 samples and executes the pending tasks stored in the buffers 35 every 500 msec. Of course, the frequency at which the processor 200 samples the buffers 35 may be varied depending on system traffic and needs. Upon periodically receiving information from the software system buffers 225 via lines 230 and the subclient buffers 225 via line 231, the processor 200 clears the content of each buffer 225 by way of asserting reset line 235.

Referring now to FIG. 6, a software system configuration table 275 is shown. The software configuration table 275 is maintained as part of the enterprise system 30 and serves as a way of routing communication between each software system 35 and client 40 in the network 20. The configuration table 275 is shown to be divided into three columns. The first column 277 represents each software system 35 in the network 20, the second column 279 represents each of the clients 40 with which a particular software system 35 may communicate through the enterprise system 30, and the third column 281 represents an assigned address of each of the clients 40 in the network 20. As shown in column 281, a midware programmer stores the midware address in the software system configuration table 275 for each client which is coupled to the midware 50 thereby making the subclients of each client transparent to the software system. In this manner, all communications directed to such clients is automatically routed directly to the midware 50. In the present embodiment, the midware address has been assigned to client 5, client 8, and client 9 (see FIG. 1) in each of the software systems 35. As the midware 50 may be configured to interface with any number of subclients 75, the software systems 35 are also effectively able to communicate with such subclients 75 by virtue of directing communication to a client 40 having the midware's address.

Figure 7:
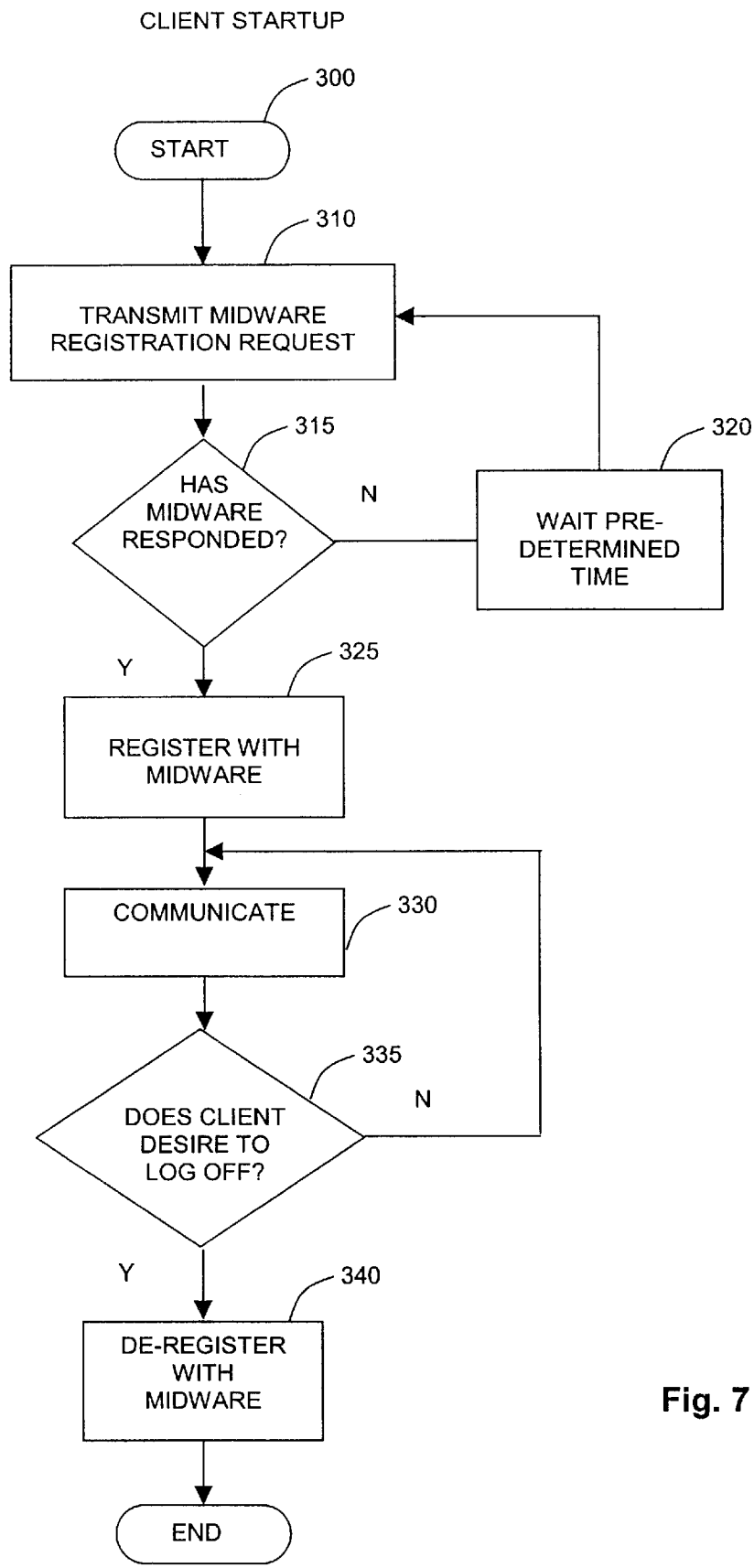
FIG. 7 is a flow chart representing the operations of a subclient in registering and de-registering with the midware in accordance with the present invention.

In order for the midware 50 to recognize whether a particular subclient is currently active, each subclient 75 of the present embodiment is configured to register with the midware 50 at startup and to de-register with the midware 50 upon the subclient 75 becoming inactivated or otherwise taken off line. The registration and de-registration routine for each subclient 75 is depicted in FIG. 7. More particularly, following startup at step 300, the subclient 300 proceeds to step 310 where the subclient 50 transmits a registration request to the midware 50. For example, if the subclient 75 is a mobile terminal 98, then the subclient 75 wirelessly transmits the registration request to the midware 50 via the access point 125 with which the mobile terminal 98 is currently registered. Alternatively, if the subclient is 75 is physically coupled to the midware 50 as with subclients 9a and 9b (FIG. 4), then the subclient 75 directly sends the registration request to the midware 50 via the particular subclient's direct physical connection 37, 38. Following transmission of the registration request, the subclient 75 in step 315 determines whether a response has been received from the midware 50 within a time out period. If no response has been received, the subclient 75 proceeds to step 320 where the subclient 75 waits a predetermined period of time before returning to step 310 and re-transmitting the registration request.

If, however, in step 315 the subclient 75 has received a response from the midware 50, the subclient 50 proceeds to step 325 where the subclient 75 registers with the midware 50 and responds to any information queries. For instance, prior to completing registration the midware 50 may request that an operator of the subclient 75 enter a user name and password in order to authenticate user access. Once all such requests are responded to by the operator, the subclient 75 registration process with the midware 50 is complete and the subclient 75 and midware may communicate with one another as depicted by step 330. During communication with the midware 50, the subclient 75 in step 335 continually monitors itself to determine whether an operator initiates a log-off routine. If an operator has not initiated a log-off routine, the subclient 75 returns to step 330 and maintains the communication session with the midware 50. If, however, in step 335 the an operator has initiated a log-off routine, the subclient 75 continues to step 340. In step 340, the subclient 75 transmits a de-registration request to the midware 50 indicating to the midware 50 that the subclient 75 is about to become inactive. Following transmission of the de-registration request, the communication session between the subclient 75 and midware 50 is ended.

Figure 8:
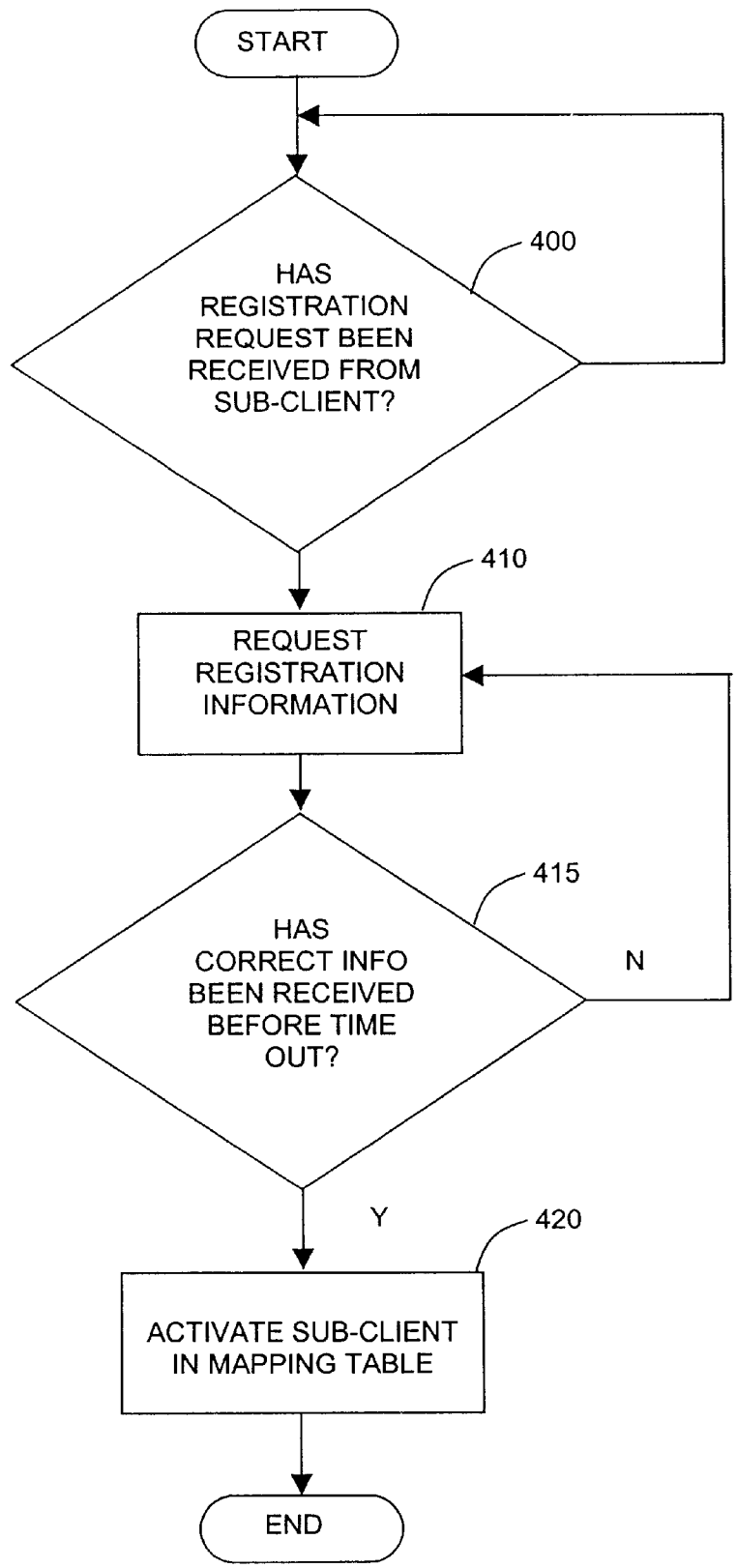
FIG. 8 is a flow chart representing the operations of the midware in registering a subclient in accordance with the present invention.

Turning now to FIG. 8, the operations of the midware processor 200 during registration of a subclient 75 to the midware 50 is depicted. In step 400, the midware processor 200 determines whether it has received a registration request from any subclient 75. If no registration requests have been received, the midware processor 200 returns to step 400. If a registration request is received, the midware processor 200 proceeds to step 410. In step 410, the midware processor 200 requests any additional information needed prior to registering the subclient 75 with the midware 50. For instance, as briefly mentioned above, the midware processor 200 may be configured to request a user ID and password prior to registering the subclient 75. Following step 410, the midware processor 200 continues to step 415, where it is determined if the information requested is received before a time out period and if so, if the received information is correct. If the information received is deemed incorrect or is not received prior to the time out period, the midware processor 200 returns to step 410 where the information is again requested. If, however, the correct information is received prior to the time out period in step 415, the midware processor 200 proceeds to step 420. In step 420, the registration with the subclient 75 is complete and the midware processor 200 activates the newly registered subclient 75 in the midware's task specific mapping table 600, as described in more detail below with respect to FIG. 11.

Figure 9:
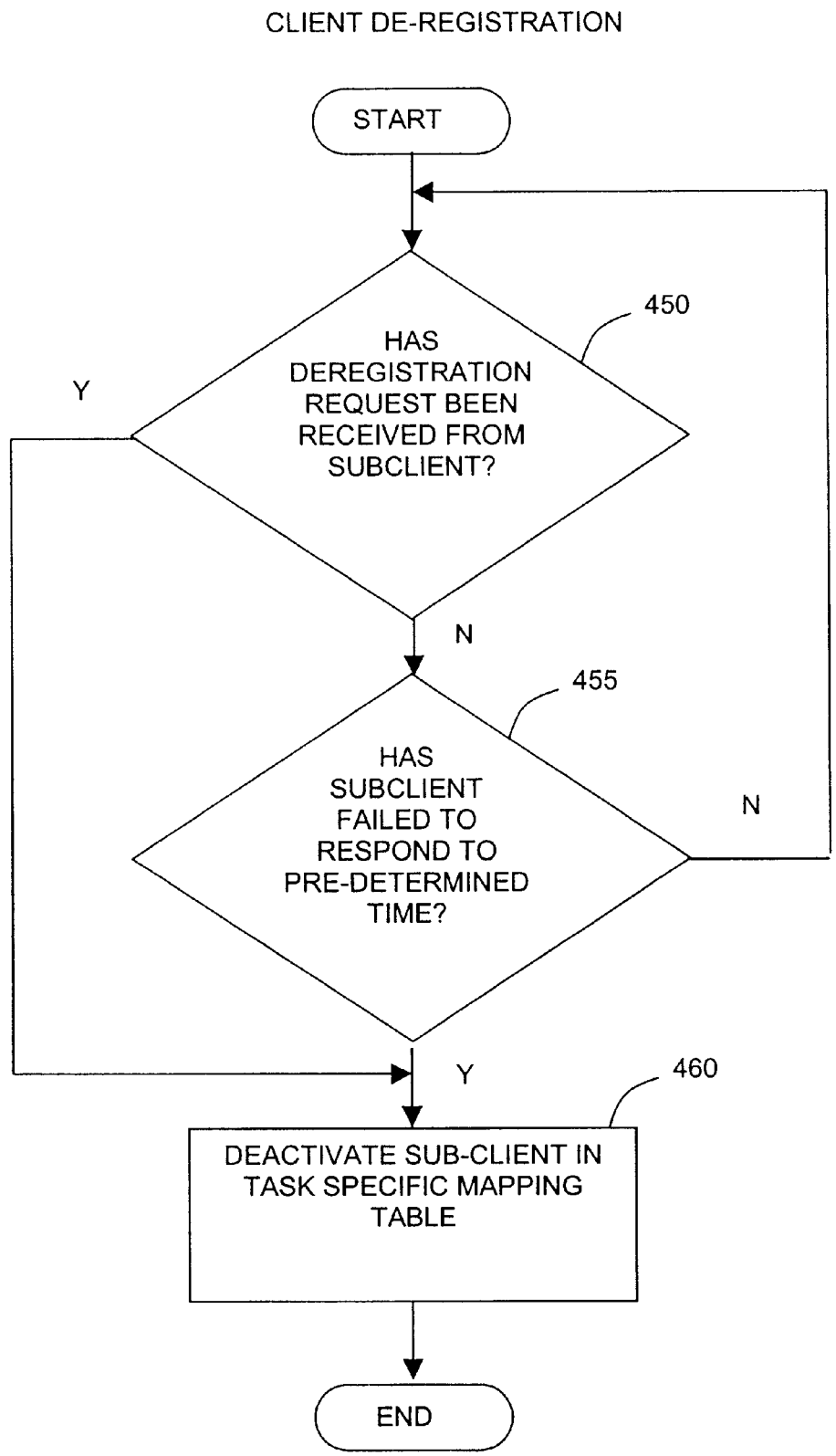
FIG. 9 is a flow chart representing the operations of the midware in de-registering a subclient in accordance with the present invention.

Turning now to FIG. 9, the operation of the midware processor 200 during de-registration of a subclient 75 to the midware 50 is depicted. More particularly, at step 450 the midware processor 200 determines whether a de-registration request has been received from a subclient 75. If a de-registration packet has been received, the midware processor 200 proceeds to step 460 where the subclient 75 transmitting the de-registration request is deactivated in the task specific mapping table 600 and communication between the subclient 75 and the midware 50 is ended. If, however, in step 450 a de-registration request is not received, the midware processor 200 proceeds to step 455. In step 455, the midware processor 200 determines whether the midware 50 has been unable to reach a particular subclient 75 for a predetermined period of time. For example, the midware processor 200 may be attempting to forward to a particular subclient 75 information received by the midware 50 from one or more software systems 35. If, however, the midware processor 200 is unable to contact the subclient 75 for the predetermined period of time the midware processor 200 assumes that the subclient 75 has been turned off without de-registering. Alternatively, if the subclient 75 is a mobile terminal 98, it may be that the subclient 75 has been moved out of communication range. Regardless, if the midware processor 200 determines that a response has not been received from the particular subclient 75 within the predetermined period of time, the midware processor 200 continues to step 460 where the subclient 75 is deregistered from the midware 50 by virtue of deactivating the subclient 75 in the task specific mapping table 600. If, however, the subclient 75 has responded in sufficient time or if the predetermined period of time has not expired, the midware processor 200 returns to step 450.

Figure 10:
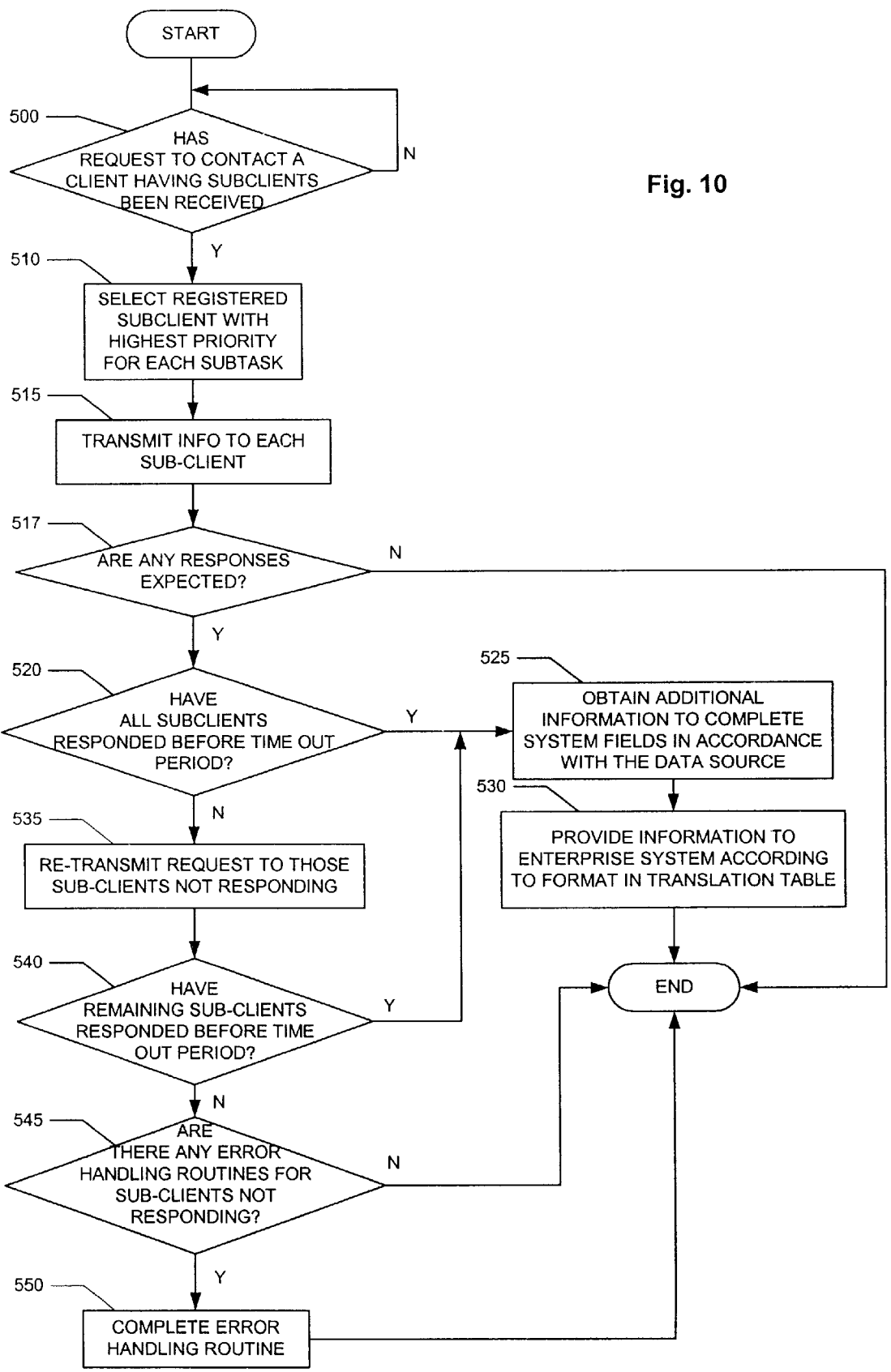
FIG. 10 is a flow chart representing the operations of the midware in routing communications originating from one or more software systems in accordance with the present invention.

Referring now to FIG. 10, there is depicted the operations of the midware processor 200 in performing a task involving communications received from one or more software systems 35 and destined to a client represented by one or more subclients 75. In step 500, the midware processor 200 determines whether it has received any requests to communicate with a client 40 coupled thereto. For instance, in the present embodiment, the midware processor 200 determines whether any software system 35 is attempting to communicate with clients c5, c8, and/or c9. In order to determine if any requests have been received to communicate with such clients, the midware processor 200 periodically checks for requests pending on line 230 (FIG. 5). As mentioned above, in the present embodiment, the midware processor 200 is configured to check for requests every 500 msec. If no requests to communicate with the clients 40 represented by the midware 50 are pending, the midware processor 200 returns to step 500. If, however, in step 500 the midware processor 200 determines one or more of such requests are pending, the midware processor 200 proceeds to step 510.

In step 510, the midware processor 200 accesses its task specific mapping table 600 which is stored in memory 210 (FIG. 5) to select the appropriate subclients 75 to perform the specified task or tasks requested by the software system(s) 35. More particularly, as seen in FIG. 11, the task specific mapping table 600 includes a column 605 of all known tasks handled by the midware 50. In particular there is shown entries for task 1 through task (n), where n represents the total number of tasks handled by the midware 50. As discussed above with respect to FIG. 2, the tasks may involve communications received from a software system 35, a client 40, a subclient 75, and/or other devices in the network 20. Further, some of the tasks entered in column 605 may represent a task which corresponds to a combination of tasks which need to be performed in the event two or more devices place requests to the midware 50 at the substantially the same time. It will be appreciated, however, that rather than entering a single task in the task specific mapping table 600 for each combination of tasks requested of the midware 50, the midware may alternatively handle both tasks individually. Also as discussed above with respect to FIG. 2, each task has associated therewith a data structure which the midware 50 expects to see when called upon to do that particular task. The data structure is stored in column 610 of the task specific mapping table 600.

As shown in column 615 of the task specific mapping table 600, each task has associated therewith one or more subtasks. Similar to the lists of tasks stored in column 610, the subtasks are each prestored in the task specific mapping table 600 and provides the midware 50 with information on how a given task is to be divided. For instance, as shown in column 615, task 1 is divided into three subtasks, namely subtask 1, subtask 2, and subtask 3. As discussed above with respect to the examples provided in FIG. 2, the purpose of each subtask is typically to either obtain a portion of the complete information needed to accomplish the task at hand and/or to communicate a portion of information to a particular device.

With respect to each subtask in column 615, there is stored in column 620 a list of authorized subclients 75 which may perform the subtask at hand. For instance, with respect to task 1, subtask 1, the authorized subclients 75 for performing subtask 1 are subclients 5*a* and 5*b*. Similarly, with respect to task 1, subtask 2, the authorized subclient 75 for performing subtask 2 is subclients 5*a*, 5*b*, and 5*c*. In some instances there may only be one authorized sub-client 75 to perform a subtask as shown with respect to task 1, subtasks 1 and 2. Further, in some instances the authorized subclients may include two subclients 75 from different clients 40 as shown with respect to task 4, subtask 1. Thus, despite the fact that a particular software system 35 requests to communicate with a single client (e.g. client 5), the midware 50 may be programmed to retrieve the information requested from subclients 75 of various different clients 40 depending on which subclients 75 are stored in the task table for performing the subtasks at hand. Further, it will be appreciated that certain tasks may be accomplished without communicating with a subclient 75 or a software system 35. For example, this is shown with respect to task 1, subtask 3 and task 2, subtask 1 in which the information is obtained from an internal and external table, respectively.

In order to prioritize the order in which the midware processor 200 selects a particular subclient 75 or subsystem 35 to perform a subtask, the subclients 75 are entered into column 620 in order of highest priority first. Thus, for example, with respect to task 1, subtask 1, subclient 5*a* is of higher priority than subclient 5*b*. Optionally, the midware processor 200 may be programmed to dynamically reprioritize the priority level of each subclient based on criteria such as the quantity of tasks currently queued for a particular subclient, the location of the subclient, the number of errors received in communicating with the subclient, etc.

In order for the midware processor 200 to select the appropriate subclient 75 for performing each subtask, the midware processor 200 initially determines which subclients 75 listed in column 620 are currently active. As discussed above with respect to FIGS. 8 and 9, a subclient 75 is activated upon registering with the midware 50 and remains active until the subclient logs-off or fails to respond to the midware 50 within a predetermined period of time. Thus, in order to select the appropriate address of the subclient 75 to be stored in column 625 of the task specific mapping table 600, the midware processor 200 in step 510 (FIG. 10) selects the highest priority subclient 75 which is currently active for each subtask. As subclients 75 register and de-register with the midware 50, column 625 is updated accordingly.

Referring again to FIG. 10, based on the subclients 75 selected to perform each subtask in step 510, the midway processor 200 continues to step 515 where the subtasks are transmitted to the appropriate subclients 75 for the particular task at hand. Once transmitted, the midware processor 200 proceeds to step 517. In step 517, the midware processor 200 determines whether the any subtasks transmitted to the subclients 75 are of a type which requires a response. If not, the midware processor 200 ends its operation. If, however, the midware processor 200 determines in step 517 that one or more responses are expected, the midware processor 200 proceeds to step 520. In step 520 the midware processor 200 monitors to determine whether a response has been received from each of the subclients 75 contacted for a particular task.

In order to keep track of whether each subclient 75 associated with a particular task has responded has responded to a subtask request, the midware 50 maintains a received response column 740 in a translation table 700 (FIGS. 12*a*–12*c*). More particularly, as shown in FIG. 12*a*, the translation table 700 includes an entry for each task 705 which the midware 50 is configured to handle. With respect to each task entry, the midware 50 maintains a list of entries which relate to how and when the midware 50 should respond to a task as is discussed in more detail below. The type of information stored in the translation table 700 is shown by way of example in FIGS. 12*b* and 12*c*, where FIG. 12*b* represents a task which originated from a software system 35 and FIG. 12*c* represents a task which originated from a subclient 75. Thus, in the present case, for each subclient 75 associated with a particular task, the translation table 700 stores in its received response column 740 whether the subclient 75 has responded to the most recent subtask request. If after a predetermined period of time, the midware processor 200 determines that all the subclients 75 for a particular task have not responded, the midware processor proceeds to step 535.

In step 535, the midware processor 200 re-transmits the subtask request to those subclients 75 which have not yet responded to the initial request transmitted in step 515. Next, in step 540 the midware processor 200 again waits to determine whether the remaining subclients 75 have responded before a time out period. If one or more subclients 75 selected to perform the subtasks of a given task do not responded before the time out period in step 540, or if a response is incomplete in any way, the midware processor 200 proceeds to step 545 to determine if there are any error handling routines. More particularly, referring again to the translation table 700 of FIG. 12*b*, for each subclient 75 there may be associated one or more error codes stored in column 745 and a corresponding number of error handling routine stored in column 750. If there are error handling routines associated with a particular subclient, then the midware processor 200 proceeds to step 550. In step 550, depending on the particular error occurring in attempting to obtain information from a subclient 75 an appropriate error handling routine is invoked by the midware processor 200. For instance, error code 1 may represent the error handling routine to be invoked if a particular subclient only provided the midware 50 with a portion of the information requested. In such a situation, the error handling routine may be configured to have the midway processor 200 re-transmit a request to the subclient 75 requesting the missing information. Alternatively, the error handling routine may be configured to place filler data in the fields not completed by the subclient 75. Of course, a variety of other error codes and corresponding error handling routines may be stored in the software translation table 700 as desired for each subclient 75. Following completion of the error handling routine in step 550, or following a determination that there are no error handling routines in step 545, the midware processor 200 ends its routine.

Continuing to refer to FIG. 10, if in step 520 or step 540 the midware processor 200 determines that all of the subclients 75 contacted to complete a given task have responded, the midware processor 200 continues to step 525. In step 525, the midware processor 200 obtains any additional information needed to complete all of the fields of the task at hand. The location of the information needed to complete all fields not already at the midware 50 is shown in column 735 of the translation table 700 (FIG. 12*b*). For example, as depicted in FIG. 12*b*, fields S1 and S2 are obtained from subclient 5a while fields S3 and s4 are obtained from subclient 5b. The additional fields may be obtained from one of a variety of different sources. For instance, fields D1, D2, and D4 were each communicated to the midware with the original task request as shown in FIG. 11, column 610. Additional fields may be obtained from one or more tables prestored in the midware memory 210, from external tables retrieved by the midware processor 200 or other locations. Upon acquiring the additional information, the midware processor 200 proceeds to step 530.

In step 530, the midware processor 200 provides a response to the software systems 35 or other devices in accordance with the information stored in columns 715 and 720 of the software translation table 700 (FIG. 12a). More particularly, the translation table 700 maintains a predefined list of devices which are to be responded to as depicted in column 715. Further, the translation table 700 maintains column 720 indicating the type of system with which the midware processor 200 is to respond so that the midware processor 200 may properly format the response. Thus, for example, upon obtaining all of the information requested by task 1, columns 715 and 720 indicate to the midware processor 200 that the report table 1000 (FIG. 14) should receive two different data structures according to the fields shown in column 730 of table 12b. Further, the midware 50 should forward to the pharmacy software system 35b in 3270 Emulation format the respective data structure shown in column 730. Similarly, the midware 50 should forward to the accounting software system 35a in ODBC format the data respective data structure shown in column 730. Of course, the midware processor 200 may be configured to communicate information according to other known formats such as HL7 and others as is well known in the art.

Figure 13:
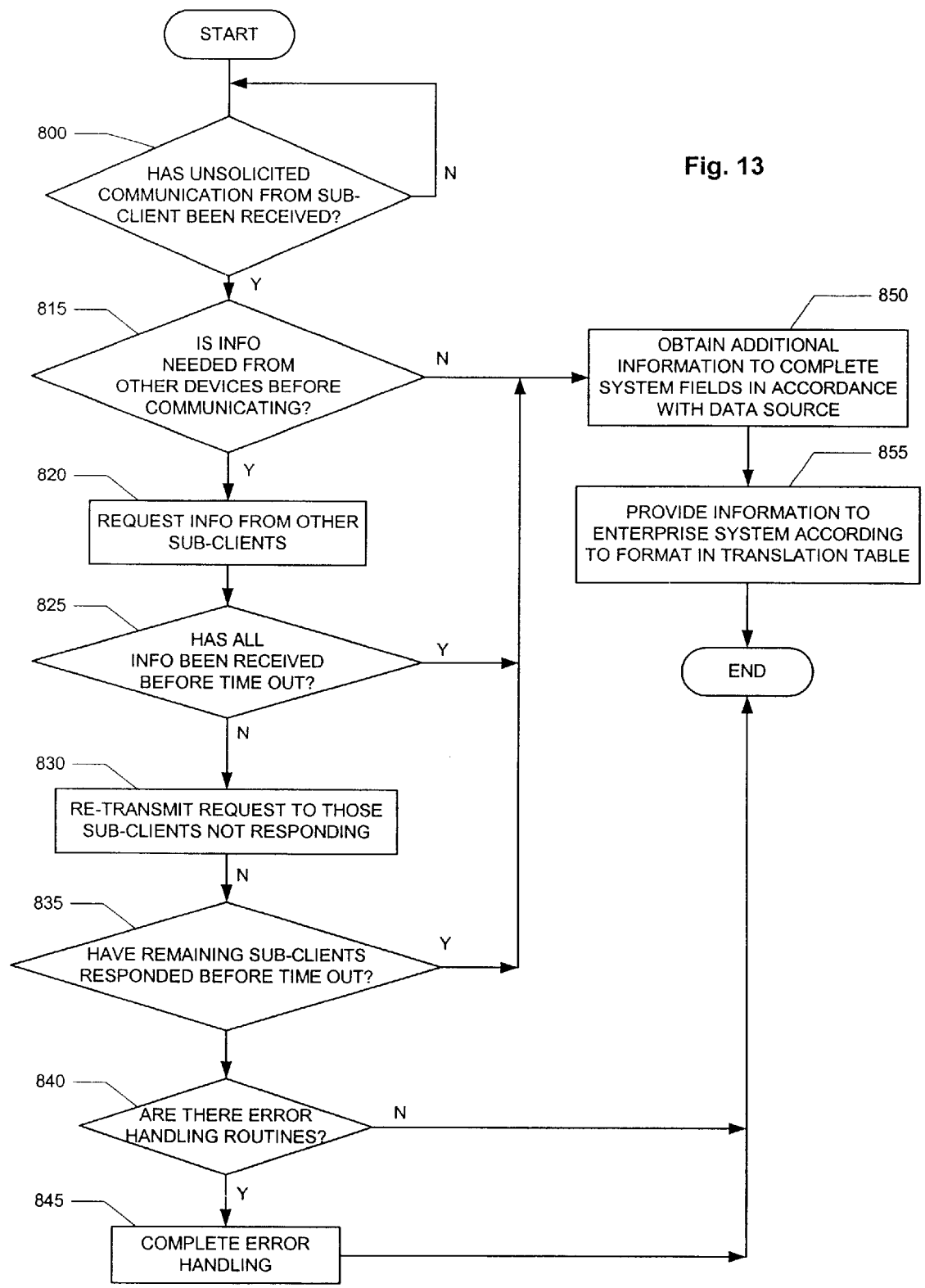
FIG. 13 is a flowchart representing the operations of the midware in routing unsolicited communications originating from one or more subclients in accordance with the present invention.

Referring now to FIG. 13, the operations of the midware 50 is shown in which the task to be performed results from unsolicited messages from one or more subclients 75 for routing to one or more software systems 35 as is the case with task 2. Beginning at step 800, the midware processor 200 determines whether any unsolicited communications from a subclient 75 has been received. If the midware processor 200 determines that no unsolicited communications have been received, the midware processor 200 returns to step 800. If however, the midware processor 200 determines that an unsolicited communication has been received, the midware processor 200 proceeds to step 815. In step 815, the midware processor 200 determines if additional information is needed from any device prior to completing the task at hand. For instance, with respect to task 2 shown in FIG. 12c, the nursing software system 35c is needed to respond to the midware 50 in order to obtain field D7 as shown with respect to columns 735 and 740. It will also be appreciated that there may be instances where a task initiated by a subclient 75 requires input from other subclients 75 before responding to the device listed in column 720 for that particular task. Thus, if in step 815 the midware processor 200 determines that all of the fields needed to respond to the devices associated with a given task are available, then the midware processor 200 proceeds to step 850. If, however, the midware processor 200 determines that additional fields are needed prior to responding to the devices, then the midware processor 200 proceeds to step 820.

In step 820, the midware processor 200 determines which fields of information from column 730 (FIG. 12c) are missing and then sends out a request to each of the corresponding devices shown in column 735 to forward the missing information. Following step 820, the midware processor 200 in step 825 determines if all of the requests for information have been responded to before a predetermined period of time. If all of the requests for information have not been responded to before the predetermined period of time, the midware processor 200 proceeds to step 830. In step 830, the midware processor 200 re-transits a request for information directed to those subclients 75 which have not responded to the request transmitted in step 820. Following the re-transmitted request(s), the midware processor 200 in step 835 again determines if all of the requests have been responded to prior to a predetermined time out period. If all of the requests still have not been responded to, the midware processor 200 proceeds to step 840 where the midware processor 200 determines if there are any error handling routines as shown in columns 745 and 750 of FIG. 12c. If there are any error handling routines, the midware processor 200 selects the appropriate error code and proceeds to step 845 where the corresponding error handling routine is executed. Following completion of the error handling routine in step 845, or if no error handling routines is available as determined in step 845, the midware processor 200 ends its routine.

If the midware processor 200 determines in any of steps 815, 825, or step 835 that all of the information needed to communicate with the devices associated with a particular task has been received, the midware processor 200 proceeds to step 850. In step 850, the midware processor 200 obtains any additional information needed to complete the fields shown in column 725. Finally, in step 855 the midware processor 200 provides all the information associated with a particular task to the corresponding device shown in column 715 in the appropriate data structure as defined by column 730.

Turning now to FIG. 14, there is shown a series of report tables 1000 which are maintained in memory 210 of the midware 50. Each report table 1000 is continually updated with information related to a specified transaction being tracked as provided in column 1010. More particularly, with respect to each table 1000, there is included up to "n" columns/fields which are tracked and updated by the midware processor 200 on an ongoing basis. In order to maintain each table 1000 with accurate information, the midware processor 200 is configured to review and distinguish communications routed through the midware 50 for information related to the transactions being tracked by each table 1000. For instance, if monitoring for blood pressure data, the midware processor 200 reviews all communication for field D7 discussed above with respect to FIG. 2. If found, the communication is then parced according to the fields being stored in the table 1000. It will be appreciated that the communications received by the midware may correspond to communications between a subclient 75 and host computer 115, 116 (FIG. 5), a subclient 75 and other subclients 75, between a subclient 75 and a software system 35, and between two or more software ware systems 35. If a transaction being tracked in found, the midware processor 200 automatically enters the associated fields in the appropriate columns and row of the report table 1000. For instance, with respect to report table 1100, a hospital may desire to track the number of blood tests administered during a given time period. In doing so, the hospital may also desire to track the subclient 75 associated with the administration of each blood test 1020, the time and date the blood test was administered 1030, the name of the patient 1040, and other relevant information 1050. Thus, each time the midware processor 200 receives communication related to a blood test, the midware processor 200 automatically enters the desired information into the blood test table 1100. Similarly, information related to the other report tables 1000 is also automatically entered according to the fields being tracked.

Figure 15:
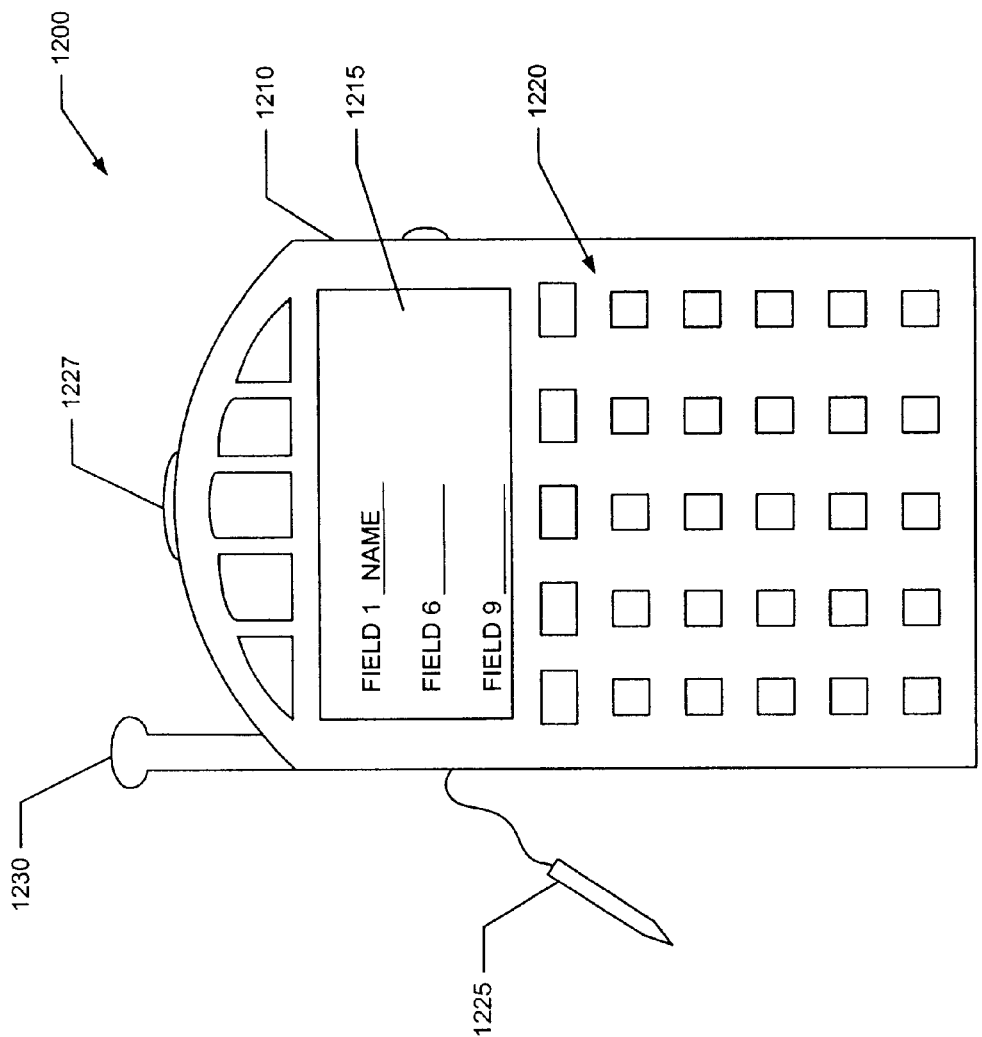
FIG. 15 is a front plan view of a thin mobile device in accordance with the present invention.
Figure 16:
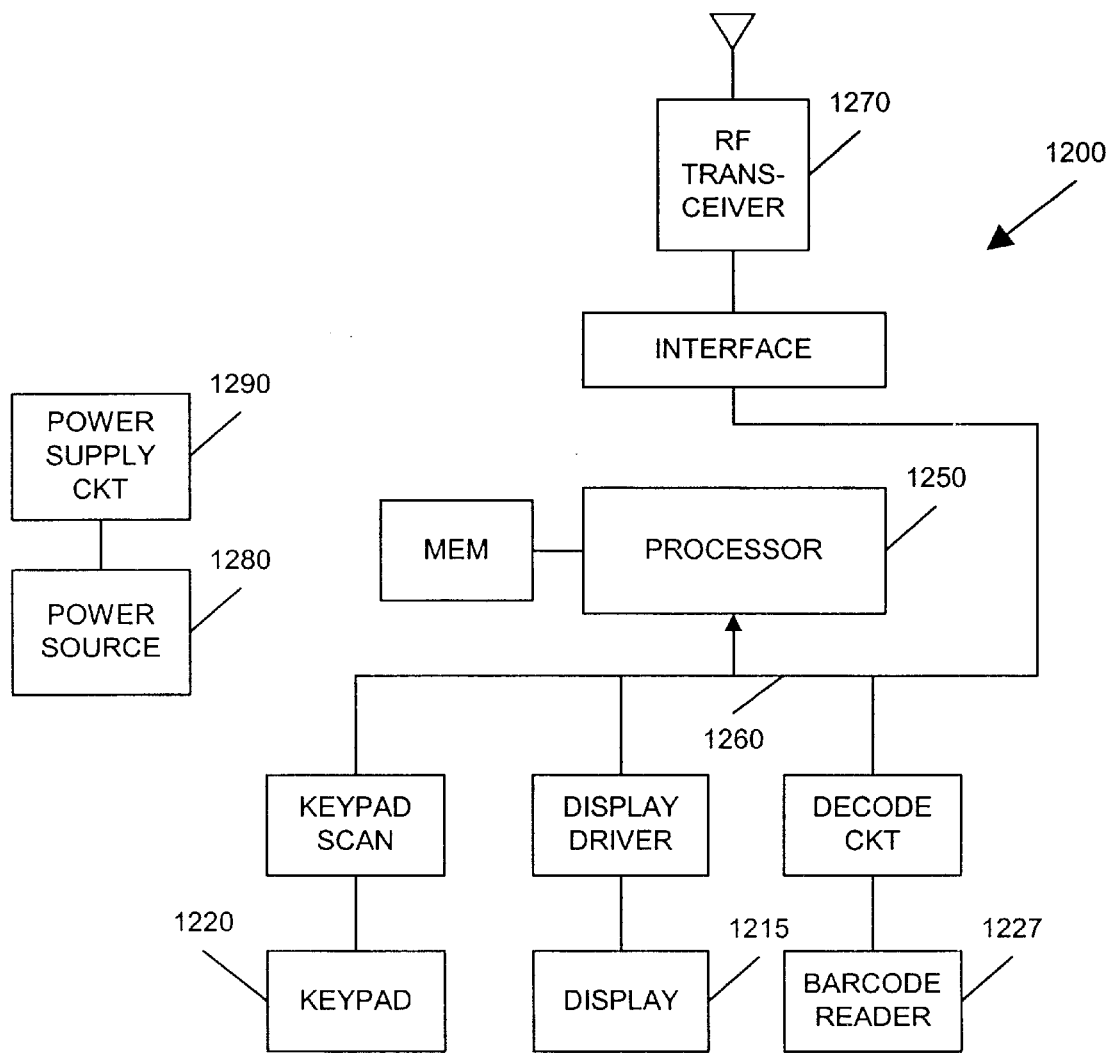
FIG. 16 is a block diagram of the circuitry of the thin mobile device in accordance with the present invention.

Turning now to FIGS. 15 and 16 an embodiment of a mobile terminal 98 in accordance with the present invention is depicted in which the mobile terminal 98 serves as a thin device 1200. As will be explained in more detail below, a mobile terminal of the present embodiment is termed a thin device 1200 when a large percentage (e.g. >50%) of a mobile terminal's processing and storage is handled by the midware processor 200 and memory 210 (FIG. 5). In such situations, the mobile terminal may operate using a reduced amount of circuitry and processing power, thereby making the mobile terminal less expensive, light weight, and less power consumptive.

As shown in FIG. 15, the thin device 1200 includes a portable housing 1210 having a pressure sensitive display screen 1215 and a keypad 1220 disposed therein. Further, the thin device 1200 includes an electronic pen 1225 electrically tethered to the portable housing 1210 for inputting commands via the display screen 1215. A bar code reader 1227 is disposed along a top portion of the portable housing 1210 and allows for reading of 1-D and 2-D bar codes as is known in the art. An antenna 1230 coupled to the portable housing 1210 allows for the wireless transmission and receipt of data.

As best seen in FIG. 16, the internal components of the thin device 1200 is shown in more detail. A processor 1250 couples to a bus 1260 and serves to communicate with processor 210 of the midware 50 via RF transceiver 1270 for controlling the operations of the thin device 1200. A memory 1275 also couples to the processor 1250 and serves to store data and executable code. The keypad 1220 couples to the processor 1250 via a keypad scan circuit 1280 through which the processor 1250 determines when a key on the keypad 1220 is depressed. The display 1215 couples to the processor 1250 through display driver circuit 1285 which functions to activate and deactivate appropriate pixels of the display screen 1215 to produce a desired message. The bar code reader 1227 couples to processor 1250 via decode circuitry 1290. In the present embodiment, the decode circuit 1290 serves to decode a 1-D or 2-D bar code into its underlying code format such as ASCII code. However, in order to minimize circuitry in the thin device 1200, the parsing of the decoded bar code data is performed by the barcode parse circuit 212 coupled to the midware processor 200 (FIG. 5). Power is provided to the thin device 1200 via power source 1280 and is distributed to the components of the thin device via power control circuit 1290.

The invention has been described with reference to the preferred embodiments. Obviously, modifications and alterations will occur to others upon reading and understanding the preceding detailed description. For instance, while the embodiments discussed above refer to the midware 50 storing a variety of table related to routing of information between software systems 35 and subclients 75, it will be appreciated that the midware 50 may combine one or more table into a single table, or may store the information according to one of a variety of alternative techniques. It is intended that the invention be construed as including all such modifications and alterations.

What is claimed is:

1. A midware server for use in an enterprise computer network having an enterprise management system which integrates one or more software systems representing respective organizations in a business, and a plurality of client central computers which are accessible to personnel, the one or more software systems of the enterprise management system being preconfigured to communicate with at least one of the plurality of client central computers in accordance with a first data structure, the midware comprising:

task processing circuitry for converting at least a portion of communications received in accordance with the first data structure into a second data structure with which said one or more software systems are not configured to communicate, or for converting at least a portion of communications received in accordance with the second data structure into the first data structure;

wherein one or more wireless communication devices provided to respective one or more personnel communicate in accordance with the second data structure and collectively represent at least one of the plurality of client central computers, the collective representation being transparent to the software systems of the enterprise management system, and wherein the task processing circuitry is adapted to route communications directed to said at least one of the plurality of client central computers from said one or more software systems in accordance with the first data structure to one or more of the wireless communication devices which collectively represent said at least one of the plurality of client central computers in accordance with the second data structure, or vice versa, thereby enabling the selective addition and/or removal of one or more wireless communication devices to/from the enterprise computer network without having to reconfigure the software systems to communicate with said one or more wireless communication devices.

2. The midware server of claim 1, wherein the business is a hospital environment, and the at least one of the client central computers is a re-fill order central computer at which nurses can enter re-fill order requests, and wherein the wireless communication devices are wireless pen base computers in which nurses enter re-fill orders as they visit a patient and determine such a re-fill order is needed, and wherein the midware server collectively represents the wireless pen base computers as the re-fill order central computer to the one or more software systems.

3. The midware server of claim 1, wherein the business is a retail company, and the at least one of the client central computers is an inventory data computer at which individuals can enter inventory data, and wherein the wireless communication devices are wireless bar code readers in which individuals enter inventory data on the retail floor, and wherein the midware server collectively represents the wireless bar code readers as the inventory data central computer to the one or more software systems.

4. The midware server of claim 1, wherein the first data structure is compatible with the enterprise management system and the second data structure is compatible with a first of the plurality of wireless communication devices.

5. The midware server of claim 4, wherein the task processing circuitry converts a portion of the communications received according to the first data structure into a third data structure compatible with another of the plurality of wireless communication devices.

6. The midware server of claim 4, wherein the task processing circuitry queries at least one of the enterprise management system and another of the plurality of wireless communication devices for information to complete conversion of the first data structure into the second data structure.

7. The midware server of claim 6, wherein the task processing circuitry further includes an error handler providing the task processing circuitry with a predefined set of instructions in the event the task processing circuitry is unable to retrieve the information to complete the conversion of the first data structure into the second data structure.

8. The midware server of claim 4, wherein the task processing circuitry further includes one or more internal tables storing predefined information and the task processing circuitry accesses the one or more internal tables to obtain information to complete the conversion of the first data structure into the second data structure.

9. The midware server of claim 1, wherein the first data structure is compatible with the first of the plurality of wireless communication devices and the second data structure is compatible with the enterprise management system.

10. The midware server of claim 9, wherein the task processing circuitry queries at least one of the enterprise management system and another of the plurality of wireless communication devices for information to complete the conversion of the first data structure into the second data structure.

11. A midware server for use in an enterprise computer network having an enterprise management system which integrates one or more software systems representing respective organizations in a business, and a plurality of client central computers which are accessible to personnel, the midware comprising:
  a first communication means operatively coupling the midware server to the one or more software systems of the enterprise management system;
  a second communication means operatively coupling the midware server to at least one of the plurality of client central computers, wherein the at least one client central computer is functionally represented by a plurality of wireless communication devices coupled to the midware server via the second communication means; and
  in the case of all or part of a software communication received from the one or more software systems and directed to the at least one client central computer, first mapping means for mapping, according to a predefined criteria, all or part of the software communication to at least one of the plurality of wireless communication devices functionally representing the at least one client central computer, the at least one of the plurality of wireless communication devices being transparent to the one or more software systems; or
  in the case of individual device communications received from at least one of the plurality of wireless communication devices and directed to the one or more software systems, second mapping means for mapping, according to a predefined criteria, all or part of the individual device communications to the one or more software systems, the at least one of the plurality of wireless communication devices being transparent to the one or more software systems.

12. The midware server of claim 11, wherein the software communication received from the one or more software systems includes a task command indicative of how the software communication is to be processed by the midware server, and the first mapping means maps all or part of the software communication in accordance with a plurality of predefined subtasks representing at least a part of the task command.

13. The midware server of claim 12, wherein the business is a hospital environment, and at least one of the one or more software systems is a pharmacy software system, and wherein the task command represents a request by the pharmacy software system to receive data related to drugs administered by a doctor, and wherein the plurality of subtasks include retrieving information related to the drugs and a respective time period for which the information is sought.

14. The midware server of claim 12, wherein with respect to each of the plurality of predefined subtasks, the first mapping means maintains a predefined list of one or more wireless communication devices of the plurality of wireless communication devices authorized to perform the respective subtask.

15. The midware server of claim 14, wherein with respect to the predefined list of one or more wireless communication devices, the first mapping means assigns a priority level to each of the one or more wireless communication devices for determining which of the one or more wireless communication devices to select to perform the subtask.

16. The midware server of claim 11, wherein the predefined criteria includes whether or not a wireless communication device is currently registered to the midware server.

17. The midware server of claim 11, wherein the predefined criteria includes a priority level assigned to each wireless communication device.

18. The midware server of claim 11, wherein the one or more software systems includes a plurality of software systems, and the second mapping means maps all or part of the individual device communications to one of the plurality of software systems.

19. The midware server of claim 18, wherein the second mapping means maps all or part of the individual device communications received from at least two of the plurality of wireless communication devices.

20. The midware server of claim 11, wherein the one or more software systems includes a plurality of software systems, and the second mapping means maps all or part of the individual device communications to at least two of the plurality of software systems.

21. A midware server for use in an enterprise computer network having an enterprise management system which integrates one or more software systems representing respective organizations in a business, and a plurality of client central computers which are accessible to personnel, the midware comprising:
  a first communication means operatively coupling the midware server to the one or more software systems of the enterprise management system;
  a second communication means operatively coupling the midware server to at least one of the plurality of client central computers, wherein the at least one client central computer is functionally represented by a plurality of wireless communication devices coupled to the midware server via the second communication means; and
  in the case of all or part of a task command received from one or more software systems of the enterprise management system and directed to the at least one client central computer,
  means for mapping, according to a predefined criteria, all or part of the task command as subtasks to at least one of the plurality of wireless communication devices functionally representing the at least one client central computer, the task command representing a task to be carried out by the at least one client central computer and the subtasks representing at least part of the task, the plurality of wireless communication devices being transparent to the one or more software systems.

22. The midware server of claim 21, wherein the midware server receives responses from the wireless communication devices based on the respective subtasks, and wherein the midware server further comprises means for translating the responses from at least one data structure compatible with the plurality of wireless communication devices to at least one other data structure compatible with the one or more software systems prior to transmitting the responses to the one or more software systems.

23. The midware server of claim 22, wherein the business is a hospital environment, and wherein the at least one data structure compatible with the plurality of wireless communication devices is a drug name D1 and time period D4 for which information is sought, and the at least one other data structure compatible with the one or more software systems is the name of the drug S1 for which for which information was requested and the amount S2 of the drug administered during the time period specified in D4.

24. The midware server of claim 22, wherein the one or more software systems comprises a plurality of individual software systems, and the means for mapping is operative to map all or part of the responses to at least two of the plurality of individual software systems.

25. The midware server of claim 24, wherein the business is a hospital environment, and wherein the plurality of individual software systems comprises at least a pharmaceutical software system and an accounting software system.

26. The midware server of claim 22, wherein the responses to the one or more software systems include data obtained by the midware server in response to at least one query to other resources in the enterprise computer network.

27. The midware server of claim 26, wherein the other resources include at least one resource selected from the group consisting of other wireless communication devices, client central computers, and internal tables.

28. The midware server of claim 22, further including a queue for queuing the responses from the wireless communication devices prior to transmitting the responses to the one or more software systems.

29. A mobile terminal for use in an enterprise computer network having a midware server for communicatively interfacing one or more software systems representing respective organizations in a business with one or more client central computers each functionally represented by a plurality of wireless communication devices, the mobile terminal comprising:
   a portable housing;
   a processor disposed in the housing; and
   means for transmitting and receiving wireless communications coupled to the processor;
   wherein the mobile terminal registers with the midware server in order to transmit and receive communications with the one or more software systems through the midware server, the midware server disguising the mobile terminal as a client central computer such that the mobile terminal is transparent to the one or more software systems.

30. The mobile terminal of claim 29, further comprising a bar code reader coupled to the processor for reading a bar code image.

31. The mobile terminal of claim 30, wherein the bar code reader is a 2-D bar code reader.

32. In an enterprise network having an enterprise management system which integrates one or more software systems representing respective organizations in a business, and a plurality of client central computers communicatively coupled to the one or more software systems, the one or more client central computers being functionally represented by a plurality of wireless communication devices through a midware server, a method comprising the steps of:
   receiving at the midware server either software communications from the one or more software systems or individual device communications from a first of the plurality of wireless communication devices;
   in the case of software communications received from the one or more software systems, converting at least a portion of the software communications into a individual device data structure compatible with the first of the plurality of wireless communication devices, and transmitting the at least a portion of the software communications to the first of the plurality of wireless communication devices according to the individual device data structure; or,
   in the case of individual device communications received from the first of the plurality of wireless communication devices, converting at least a portion of the individual device communications into a software data structure compatible with the one or more software systems, and transmitting the at least a portion of the individual device communications to the one or more software systems according to the software data structure.

33. The method of claim 32, wherein, in the case of software communications received from the one or more software systems, the step of converting at least a portion of the software communications includes the step of querying at least one of the one or more software systems and another of the plurality of wireless communication devices for information needed to convert the at least a portion of the software communications into the individual device data structure; and,
   wherein, in the case of individual device communications received from the first of the plurality of wireless communication devices, the step of converting at least a portion of the individual device communications includes the step of querying at least one of the one or more software systems and another of the plurality of wireless communication devices for information needed to convert the at least a portion of the individual device communications into the software communication data structure.

34. In an enterprise network having an enterprise management system which integrates one or more software systems representing respective organizations in a business, and a client central computer communicatively coupled to the one or more software systems, the client central computer being functionally represented by a plurality of wireless communication devices through a midware server, a method comprising the steps of:
   transmitting by the enterprise network a communication destined for the client central computer;
   receiving the communication by the midware server;
   converting at least a portion of the communication to a first format compatible with a first of the plurality of wireless communication devices and another portion of the communication to a second format compatible with a second of the plurality of wireless communication devices; and
   transmitting the at least a portion of the communication to the first of the plurality of wireless communication devices in the first format and the at least another portion of the communication to the second of the plurality of wireless communication devices in the second format.

35. The method of claim 34, further comprising the steps of:

receiving a reply from at least one of the first and second of the plurality of wireless communication devices;

converting the reply into a format compatible with the one or more software systems of the enterprise management system; and transmitting to the one or more software systems the reply in the format compatible with the one or more software systems.

36. The method of claim 34, wherein the business is a hospital environment, and the client central computer is a nurse central computer at which nurses can enter information, and wherein the wireless communication devices are wireless pen base computers in which nurses enter information as they visit a patient, and wherein the one or more software systems includes a pharmacy software system, and wherein the midware server collectively represents the wireless pen base computers as the nurse central computer to the pharmacy software system, and wherein the step of transmitting by the enterprise network includes transmitting a communication request by the pharmacy software system to receive data related to a first drug and a second drug; and wherein the step of converting the at least a portion of the communication includes:

converting that portion of the communication request relating to the request for information relating to the first drug into the first format compatible with the first of the plurality of wireless communication devices, wherein the first of the plurality of wireless communication devices is a first wireless pen base computer in which a first nurse can enter information, and converting that portion of the communication request relating to the request for information relating to the second drug into to the second format compatible with the second of the plurality of wireless communication devices, wherein the second of the plurality of wireless communication devices is a second wireless pen base computer in which a second nurse can enter information; and, wherein the step of transmitting the at least a portion of the communication includes:

transmitting that portion of the communication request relating to the first drug to the first wireless pen base computer in the first format so that the first nurse is notified of the request for information relating to the first drug, and transmitting that portion of the communication request relating to the second drug to the second wireless pen base computer in the second format so that the second nurse is notified of the request for information relating to the second drug.

37. The method of claim 36, further comprising the steps of:

receiving a reply from at least one of the first wireless pen base computer and second wireless pen base computer;

converting the reply into a format compatible with the pharmacy software system of the enterprise management system; and transmitting to the pharmacy software system the reply in the format compatible with the pharmacy software system.

38. The method of claim 37, wherein the reply received from the at least one of the first wireless pen base computer and second wireless pen base computer is the name of the respective first and second drug for which information was requested and an amount of the respective first and second drug administered.

* * * * *